US006921848B2

(12) United States Patent
Chory et al.

(10) Patent No.: US 6,921,848 B2
(45) Date of Patent: Jul. 26, 2005

(54) GENES INVOLVED IN BRASSINOSTEROID HORMONE ACTION IN PLANTS

(75) Inventors: Joanne Chory, Del Mar, CA (US); Zhiyong Wang, Palo Alto, CA (US)

(73) Assignee: The Salk Institute for Biological Studies, La Jolla, CA (US)

( * ) Notice: Subject to any disclaimer, the term of this patent is extended or adjusted under 35 U.S.C. 154(b) by 218 days.

(21) Appl. No.: 09/995,938

(22) Filed: Nov. 27, 2001

(65) Prior Publication Data

US 2003/0150026 A1 Aug. 7, 2003

(51) Int. Cl.$^7$ ..................... C12N 12/29; C12N 15/82; A01H 5/00
(52) U.S. Cl. .................. 800/298; 800/320; 800/306; 236/23.1; 236/23.6; 435/320.1; 435/419
(58) Field of Search ................. 800/298, 320, 800/306, 278, 287, 290; 536/23.1, 23.6; 435/419, 320.1, 468

(56) References Cited

U.S. PATENT DOCUMENTS 4,407,956 A    10/1983   Howell

OTHER PUBLICATIONS

Bowie et al, Science 247:1306–1310, 1990.*
McConnell et al, Nature 411 (6838):709–713, 2001.*
Altschul, et al., *J. Mol. Biol.*, 215:403, 1990.
Altschul, et al., *Meth Enzymol.*, 266:460, 1996.
Altschul, et al., *Nature Genet.*, 6:119, 1994.
Altschul, et al., *Nucleic Acids Res.*, 25:3389, 1997.
Asami, et al., *Plant Physiol.*, 123:93, 2000.
Atanassova, et al., *Plant J.*, 2:291, 1992.
Beato, et al., *Cell*, 83:851, 1995.
Bitter, et al., *Methods in Enzymology*, 153:516, 1987.
Brisson, et al., *Nature*, 310:511, 1984.
Broglie, et al., *Science*, 224:838, 1984.
Coruzzi, et al., *EMBO J.*, 3:1671, 1984.
De Framond, *Biotechnology*, 1: 262, 1983.
Devereux, et al., *Nucl. Acids Res.*, 12:387, 1984.
Friedrichsen, et al., *Plant Physiol.*, 123: 1247, 2000.
Fromm, et al., *Proc. Natl. Acad. Sci., U.S.A.*, 82:5824, 1985.
Grove, et al., *Nature*, 281:216 1979.
Gurley, et al., *Mol. Cell. Biol.*, 6:559, 1986.
Harlow and Lane, *Antibodies: A Laboratory Manual*, only title page.

He, et al., *Science*, 288: 2360, 2000.
Hershey, et al., *Plant Mol. Biol.*, 17:679, 1991.
Hoekema, et al., *Nature*, 303:179, 1983.
Horsch, et al., *Science*, 227:1229, 1985.
Mansour Ioualalen, *C. R. Acad. Sci. Paris*, 316:1194 (1993).
Ito, et al., *Plant Mol. Biol.*, 24:863, 1994.
Jaye, et al., *Nucl. Acid Res.*, 11:2325, 1983.
Klee, et al., *Annu. Rev. Plant Physiol.*, 38:467, 1987.
Klein, et al., *Nature*, 327:70, 1987.
Kohler, et al., *Nature*, 256:495, 1975.
Li and Chory, *Cell*, 90, 929–938, 1997.
Lukowitz et al., *Plant Physiol.*, 123, 795–805, 2000.
Madden, et al., *Meth. Enzymol.*, 266:131, 1996.
Mandava, et al., *Ann. Rev. Plant Physiol. Plant Mol. Biol.*, 39:23, 1988.
Mangelsdorf, et al., *Cell*, 83:835, 1995.
Maniatis et al., Molecular Cloning A Laboratory Manual, Cold Spring Harbor (*1989*), title + table of contents.
Martinez, et al., *Proc. Natl. Acad. Sci. USA*, 89:7360, 1992.
Medford, et al., *Plant Cell*, 3:359, 1991.
Mett, et al., *Proc. Natl. Acad. Sci., U.S.A.*, 90:4567 (1993), NY, Section VIII, pp. 421–463.
Odell, et al., *Nature*, 313:810, 1985.
Rogers et al., *Methods For Plant Mol. Biol.*, 423–463 (1988).
Schena, et al., *Proc. Natl. Acad. Sci., U.S.A.*, 88:10421, 1991.
Schmidt, et al., *Front Neuroendocrinol*, 21:57, 2000.
Severin, et al., *Plant Mol. Biol.*, 15:827, 1990.
Takamatsu, et al., *EMBO J.*, 6:307, 1987.
Tatusova, et al., *FEMS Microbiol Lett.*, 174:247, 1999.
Velten, et al., *EMBO J.*, 3:2723, 1984.
Wallace, et al., *Nucl. Acid Res.*, 9:879, 1981.
Wang, et al., *Nature*, 410: 380, 2001.
Wehling, *Annu. Rev. Physiol.*, 59:365, 1997.
Weigel, et al., *Plant Physiol.*, 122:1003, 2000.
Wissenbach, et al., *Plant Journal*, 4:411, 1993.

* cited by examiner

Primary Examiner—Amy J. Nelson
Assistant Examiner—Stuart F. Baum
(74) Attorney, Agent, or Firm—Morrison & Foerster LLP

(57) ABSTRACT

The present invention provides a BZR1 gene and an altered gene, bzr1-D, involved in the brassinosteroid response pathway. The expression of BZR1 genes in transgenic plants causes such plants to become significantly larger and more robust than their wild-type counterparts, thus increasing plant yields.

12 Claims, No Drawings

SEQUENCE LISTING

<160> NUMBER OF SEQ ID NOS: 14

<210> SEQ ID NO 1
<211> LENGTH: 2687
<212> TYPE: DNA
<213> ORGANISM: ARABIDOPSIS THALIANA

<400> SEQUENCE: 1

```
actttagttt tgcctaattc atcgaaccct ctgattcatt ccaaatgttt cccaactcgc      60
gttgatggtt cgggttcctc tgcttttaag acattagtta catgctcctg cactttctac     120
```

-continued

```
aaaataaacg tcataatcca aaaatattac atgatcatac atcatatatg ccgccgaacc     180
ttgttatggg acaaactcgt aaacccctttt ttccttttat gttcaatgaa ctatacaagt    240
tttggttatg aatacataaa taatgatgga cccagcaatt aatccaaaat ttggatatta    300
gatactaaag cttaaaatca acatgtaacc aaactaaata ctttatagaa catagtaaat    360
ggtattcacc aatctttata tcatttgtaa ggtacgaaga aggtaaaaaa aagagagagc    420
cagtgtacat acaactaatc aggacaaaag tagtcaaaat tgtttctaaa gtgagatttg    480
tatgcaagaa aaaagtgata attttttaatt gaatatatca ttatgatgtt aatcacacgg    540
cttcactgta taaaataaaa ttttaaaaac caatcaaatg gtgtgttttt cggtcacaca    600
agtaagggac ccacactgaa gaaacggtcc cactgtgtct cctcctttct tttctctgta    660
ttatttggtc attactcatt ttacatactc acagaaaaaa aaaagatta gaacataaac     720
acacgttact aagcgtagtt atcctctgca ccttaacata cacctcttat attcacctca    780
cgtaatctca cccttccaaa accatgtatt tacacgtgga cgatcgatac acaagaacaa    840
tgattcttaa tatgaactca atgtacttga acacacacac gacccaattt ttacattaga    900
tgaaaaaaat attattattt gttggagaag aaagagagat tcttcttctt cgattccagc    960
gaaggaaaag cgtattcctc gtgagcacta acttctcact cctctcttct tcttcttcat   1020
cagtctacgt tcacacaatc tttcacccac ctattcaaag ctctctccgg aagtttcgag   1080
gggttggttg ttggttttcc cgatgacttc ggatggagct acgtcgacat cagcagctgc   1140
agctgcggcg gcggcagcag cggcgaggag gaagccgtcg tggagagaaa gggagaataa   1200
tcggaggaga gaaagacgga gaagagctgt agctgcgaag atatacactg ggcttagagc   1260
tcaaggtgat tataatttgc ctaaacattg tgataataat gaagtcctta aagctctttg   1320
tgttgaagct ggttgggttg ttgaagaaga tggtactact tatcgcaagg tgaagacttt   1380
ctccattttt tccagatctg agcttgtttt attgatgttt ttgatgtttg aatctgaatt   1440
cgttgatttc aattgtggtt aaatgggttt gaatctgaga atttgagggt tttctcaaag   1500
tgaatttgaa tcatcagaaa ctatggatgg atctgatttc tcaaagtgaa tttatgggtt   1560
ttcttttctaa ttttagagtt attattggta tgctaaagtc ttaatctttt atgtatgata   1620
cttggtccaa agtcattgca ttgtgtttct tttgcttacc tgtgattgat tgatgtttga   1680
ttggttattg ttttgctttt gttggagtat cagggatgca agcctttacc tggtgagata   1740
gctgggactt catctcgagt aactccatat tcatcacaga accagagccc tctttcatca   1800
gcctttcaaa gtcccatccc atcttaccaa gttagcccgt cttcttcatc attcccgagt   1860
ccttctcgcg gtgaaccaaa taacaacatg tcctctacat tcttcccttt cctcagaaat   1920
ggtggcattc cttcttctct tccttccctc agaatctcaa acagttgtcc agttacccca   1980
ccggtctcat cgccgacttc taagaacccg aaaccgttgc ctaactggga atctatcgct   2040
aagcaatcca tggccattgc taaacaatca atggcgtctt ttaattatcc tttctatgcg   2100
gtttctgcac ctgctagtcc gacacatcgc caccagtttc ataccccggc tactatacct   2160
gaatgtgatg agtctgactc ttccactgtt gattctggtc attggataag ctttcagaag   2220
tttgcacaac aacagccatt ctctgcctct atggtgccaa cctctcctac cttcaatctt   2280
gtgaaacctg cgcctcagca gatgtctcca aatactgctg ccttccaaga gattggtcaa   2340
agctctgagt ttaaatttga gaatagccaa gttaaaccct gggaaggaga gaggatacat   2400
gatgtgggta tggaggatct tgagcttaca cttggaaatg ggaaggctcg tggttgacat   2460
aaacaactag gcaaacccaa atggcatgtc attggaatat gagaaactaa tcctcttgag   2520
```

-continued

| | |
|---|---|
| tattttcttc ttcgtccagg tatttggatc tttatggaat ctcatatgtt cttcacttat | 2580 |
| tatccaaata tgctgcccaa agccttctcc atggaagcat tggagtgtta gagtggttat | 2640 |
| tcaattcatg aatttggttt caaaagcatt atttgtagat aaaaaaa | 2687 |

<210> SEQ ID NO 2
<211> LENGTH: 2687
<212> TYPE: DNA
<213> ORGANISM: ARABIDOPSIS THALIANA

<400> SEQUENCE: 2

| | |
|---|---|
| actttagttt tgcctaattc atcgaaccct ctgattcatt ccaaatgttt cccaactcgc | 60 |
| gttgatggtt cgggttcctc tgcttttaag acattagtta catgctcctg cactttctac | 120 |
| aaaataaacg tcataatcca aaatatttac atgatcatac atcatatatg ccgccgaacc | 180 |
| ttgttatggg acaaactcgt aaaccccttt tccttttat gttcaatgaa ctatacaagt | 240 |
| tttggttatg aatacataaa taatgatgga cccagcaatt aatccaaaat ttggatatta | 300 |
| gatactaaag cttaaaatca acatgtaacc aaactaaata cttatagaa catagtaaat | 360 |
| ggtattcacc aatctttata tcatttgtaa ggtacgaaga aggtaaaaaa aagagagagc | 420 |
| cagtgtacat acaactaatc aggacaaaag tagtcaaaat tgtttctaaa gtgagatttg | 480 |
| tatgcaagaa aaaagtgata attttttaatt gaatatatca ttatgatgtt aatcacacgg | 540 |
| cttcactgta taaaataaaa ttttaaaaac caatcaaatg gtgtgttttt cggtcacaca | 600 |
| agtaagggac ccacactgaa gaaacggtcc cactgtgtct cctcctttct tttctctgta | 660 |
| ttatttggtc attactcatt ttacatactc acagaaaaaa aaaagatta gaacataaac | 720 |
| acacgttact aagcgtagtt atcctctgca ccttaacata cacctcttat attcacctca | 780 |
| cgtaatctca cccttccaaa accatgtatt tacacgtgga cgatcgatac acaagaacaa | 840 |
| tgattcttaa tatgaactca atgtacttga acacacacac gacccaattt ttacattaga | 900 |
| tgaaaaaaat attattattt gttggagaag aaagagagat tcttcttctt cgattccagc | 960 |
| gaaggaaaag cgtattcctc gtgagcacta acttctcact cctctcttct tcttcttcat | 1020 |
| cagtctacgt tcacacaatc tttcacccac ctattcaaag ctctctccgg aagtttcgag | 1080 |
| gggttggttg ttggttttcc cgatgacttc ggatggagct acgtcgacat cagcagctgc | 1140 |
| agctgcggcg gcggcagcag cggcgaggag gaagccgtcg tggagagaaa gggagaataa | 1200 |
| tcggaggaga gaaagacgga gaagagctgt agctgcgaag atatacactg gcttagagc | 1260 |
| tcaaggtgat tataatttgc ctaaacattg tgataataat gaagtcctta agctcttttg | 1320 |
| tgttgaagct ggttgggttg ttgaagaaga tggtactact tatcgcaagg tgaagacttt | 1380 |
| ctccatttttt tccagatctg agcttgtttt attgatgttt ttgatgtttg aatctgaatt | 1440 |
| cgttgatttc aattgtggtt aaatgggttt gaatctgaga atttgagggt tttctcaaag | 1500 |
| tgaatttgaa tcatcagaaa ctatggatgg atctgatttc tcaaagtgaa tttatgggtt | 1560 |
| ttctttctaa ttttagagtt attattggta tgctaaagtc ttaatctttt atgtatgata | 1620 |
| cttggtccaa agtcattgca ttgtgtttct tttgcttacc tgtgattgat tgatgtttga | 1680 |
| ttggttattg ttttgctttt gttggagtat cagggatgca agcctttacc tggtgagata | 1740 |
| gctgggactt catctcgagt aactccatat tcatcacaga accagagccc tctttcatca | 1800 |
| gcctttcaaa gtcccatccc atcttaccaa gttagcccgt cttcttcatc attcccgagt | 1860 |
| cctcctcgcg gtgaaccaaa taacaacatg tcctctacat tcttcccttt cctcagaaat | 1920 |

-continued

```
ggtggcattc cttcttctct tccttccctc agaatctcaa acagttgtcc agttacccca    1980
ccggtctcat cgccgacttc taagaacccg aaaccgttgc ctaactggga atctatcgct    2040
aagcaatcca tggccattgc taaacaatca atggcgtctt ttaattatcc tttctatgcg    2100
gtttctgcac ctgctagtcc gacacatcgc caccagtttc atccctggc tactatacct    2160 gaatgtgatg agtctgactc ttccactgtt gattctggtc attggataag ctttcagaag    2220
tttgcacaac aacagccatt ctctgcctct atggtgccaa cctctcctac cttcaatctt    2280
gtgaaacctg cgcctcagca gatgtctcca aatactgctg ccttccaaga gattggtcaa    2340
agctctgagt ttaaatttga aatagccaa gttaaaccct gggaaggaga gaggatacat    2400
gatgtgggta tggaggatct tgagcttaca cttggaaatg ggaaggctcg tggttgacat    2460
aaacaactag gcaaacccaa atggcatgtc attggaatat gagaaactaa tcctcttgag    2520
tattttcttc ttcgtccagg tatttggatc tttatggaat ctcatatgtt cttcacttat    2580
tatccaaata tgctgcccaa agccttctcc atggaagcat ggagtgtta gagtggttat    2640 tcaattcatg aatttggttt caaaagcatt atttgtagat aaaaaaa              2687

<210> SEQ ID NO 3
<211> LENGTH: 3000
<212> TYPE: DNA
<213> ORGANISM: ARABIDOPSIS THALIANA

<400> SEQUENCE: 3
tgaatatcct cacatttcca tttttcgactc tctttagtaa attttgaagt agtagaatga     60
tgtagaatgt tttgtttat caatcacaca gttttgtgaa atcacgatt ccatccacta    120 ttcaagaaaa acatcaagtg gaagaaataa taaaccaaaa ccatcgcaac aaaatgcata    180
tcacgagtat agaatgaaca actacactg tcaaatactt aatttaggac ttaaacttcg    240
ctttcagaca acttggttcg gaaacttgac catccgtcat gttgatatac acaatccatc    300
tcaaatgtag tagtgaatca ctatatcagc atgtgttatc aaacgcaagt tgtcactaag    360
atcggagctt ctagttcaaa atgttgataa gtattacgaa agtacaattg aatataccaa    420
ttatacatcc aaacacgtcc atgcttctcc actcgagttc tctttggaaa tctatataat    480
ccgtcggttt ggtattttac tagttgtacg tagtgtctcc cctcatatgt attgagtctt    540
tatagtttgt tgcctcgtat acgatagaaa gtaaaggcta aaaaaccata ctatttcata    600
aagggtttat ttagttaact tttaatctaa accatgtatc actccatttt acgtatattc    660
gttttcacaa ataatctact aaataatttt gtaatgtgat aaaattaaag aataaacaca    720
tgatacataa acagtcagga caaaagtaag cactcatttt cttctattca tactatagtg    780
aaacactatt ttatttttat ccatatacta tagtgacaaa ttaatctaat cattaaatgt    840
tatgaggctc aaaacaattt gttttcttat ttaacatggc cgatcccctc ataaaccaat    900
cagatggtgt gttttccggt catactcgtg taggacccac ttcattacaa tggccccaca    960
tgtctctcta tctttttctc ctctttataa aatcagctcc ttttcttaca cagatttaga   1020
gaaacacaac ataaaacgta cttcttcttc aaaacgcgaa accacactgt aagttacgta   1080
caccaccacc tatcctcacc attcatcatc gacacgtggc tggtttaact caaatcaacg   1140
gtgaattctt tttgcttttt tattttaaat aatgaatgaa aagattcttc tataattcca   1200
gcgaagaaga aagaaaaaaa aaagcgtatt cctcgtgagc actaacttct cactcattct   1260
tcttcttcag ctgaatccaa ataccccattt ccatttttaa ccgtggtggg attgttttga   1320
gagttgaagg aagaagatga cgtctgacgg agcaacgtcg acgtcagctg cagctgcagc   1380
```

```
agcagcgatg gcgacgagga ggaaaccgtc gtggagagag agggagaaca atcggagaag    1440
agagcggcgg agaagagctg ttgcggcgaa gatttatact ggtcttagag ctcaaggtaa    1500
ctacaatctt ccaaaacatt gtgacaacaa tgaggttctt aaggctcttt gttctgaagc    1560
tggttgggtt gttgaagaag acggaactac ttatcgcaag gtcagtatca aacgcatttt    1620
tacttagatc tgatgttatc tgatgattta gctgttgaat ctgaagattt ggatttgaaa    1680
ttggtcaaat tgggattttc ttggctatga attcgaggtt tttagctgag gaagctcagt    1740
tttattctaa aattggatcg agattccttg cggagaaagt gacctttagg gttcttctta    1800
ctaatttgag aaccgaatta gctttacttt cacttggtta ctatatttag atctctcctt    1860
tagcttttga ttgattgtga cattgtgatg ttttggtat tgttctatga gcaacaggga    1920
cacaagcctc tacctggtga catggctgga tcatcttctc gagcaactcc ttactcttcc    1980
cataaccaaa gtcctctttc ttccactttt gatagcccca tcttatctta ccaagtcagt    2040
ccttcctctt cttcattccc gagtccttct cgagttggtg atccacacaa tatctccaca    2100
atcttccctt tcctcaggaa tggtggtatt ccttcatcgc ttcctccact tagaatctca    2160
aacagtgctc ctgtcactcc accagtgtca tccccaactt ctagaaaccc caaaccattg    2220
cctactgggg aatcttttac caaacaatcc atgtccatgg ctgctaaaca gtcaatgact    2280
tctttgaact cccgttttta tgcggtgtct gcacctgcca gtcctactca tcatcgccag    2340
ttccatgctc cggctactat acctgaatgt gatgagtctg actcttccac tgttgattct    2400
ggtcattgga taagctttca aaagtttgca caacaacagc cattctctgc ctctatggtg    2460
ccaacctcgc ctaccttcaa tctcgtgaaa cctgcaccac agcaattgtc tccaaacaca    2520
gcagcaatcc aagagattgg tcaaagctcc gagtttaagt ttgagaacag ccaagttaag    2580
ccatgggaag gggagaggat ccatgatgtg gctatggagg atctagagct cacgcttgga    2640
aatggtaaag ctcatagttg agatgaagta tacatgaacc tgttatgtca tgtcggaagg    2700
aaggattgga gaatgagaat tagtgtgttg ttcattcagt tcatggtttt ggttcttgtt    2760
ctagaatcga tattcattgt accagtgagt ttgtttcaca acgcattatt tgtagataga    2820
atgtttaaga tgtatgtttc tattatcatt cctttttaggt cttgaaaaca ttacaaatat    2880
attacatgat taagtggctt gaaatgtaaa ttatatatcg gatgatgaaa cagagaaaaa    2940
caagtgaggc taaaacaaag acttgggatg taataacaag atcagagagg ttaagaaaga    3000
```

<210> SEQ ID NO 4
<211> LENGTH: 1456
<212> TYPE: DNA
<213> ORGANISM: ARABIDOPSIS THALIANA

<400> SEQUENCE: 4

```
gacccaattt ttacattaga tgaaaaaaat attattattt gttggagaag aaagagagat      60
tcttcttctt cgattccagc gaaggaaaag cgtattcctc gtgagcacta acttctcact     120
cctctcttct tcttcttcat cagtctacgt tcacacaatc tttcacccac ctattcaaag     180
ctctctccgg aagtttcgag gggttggttg ttggttttcc cgatgacttc ggatggagct     240
acgtcgacat cagcagctgc agctgcggcg gcggcagcag cggcgaggag gaagccgtcg     300
tggagagaaa gggagaataa tcggaggaga gaaagacgga gaagagctgt agctgcgaag     360
atatacactg gcttagagc tcaaggtgat tataatttgc ctaaacattg tgataataat      420
gaagtcctta agctcttttg tgttgaagct ggttgggttg ttgaagaaga tggtactact     480
```

-continued

```
tatcgcaagg gatgcaagcc tttacctggt gagatagctg ggacttcatc tcgagtaact    540
ccatattcat cacagaacca gagccctctt tcatcagcct ttcaaagtcc catcccatct    600
taccaagtta gcccgtcttc ttcatcattc ccgagtcctt ctcgcggtga accaaataac    660
aacatgtcct ctacattctt cccttcctc agaaatggtg gcattccttc ttctcttcct     720
tccctcagaa tctcaaacag ttgtccagtt accccaccgg tctcatcgcc gacttctaag    780
aacccgaaac cgttgcctaa ctgggaatct atcgctaagc aatccatggc cattgctaaa    840
caatcaatgg cgtcttttaa ttatcctttc tatgcggttt ctgcacctgc tagtccgaca    900
catcgccacc agtttcatac cccggctact ataccgaat gtgatgagtc tgactcttcc     960
actgttgatt ctggtcattg gataagcttt cagaagtttg cacaacaaca gccattctct   1020
gcctctatgt gccaacctc tcctacctcc aatcttgtga aacctgcgcc tcagcagatg    1080
tctccaaata ctgctgcctt ccaagagatt ggtcaaagct ctgagtttaa atttgagaat   1140
agccaagtta aaccctggga aggagagagg atacatgatg tgggtatgga ggatcttgag   1200
cttacacttg gaaatgggaa ggctcgtggt tgacataaac aactaggcaa acccaaatgg   1260
catgtcattg gaatatgaga aactaatcct cttgagtatt ttcttcttcg tccaggtatt   1320
tggatcttta tggaatctca tatgttcttc acttattatc caaatatgct gcccaaagcc   1380
ttctccatgg aagcattgga gtgttagagt ggttattcaa ttcatgaatt tggtttcaaa   1440
agcattattt gtagat                                                  1456
```

<210> SEQ ID NO 5
<211> LENGTH: 1456
<212> TYPE: DNA
<213> ORGANISM: ARABIDOPSIS THALIANA

<400> SEQUENCE: 5

```
gacccaattt ttacattaga tgaaaaaaat attattattt gttggagaag aaagagagat     60
tcttcttctt cgattccagc gaaggaaaag cgtattcctc gtgagcacta acttctcact    120
cctctcttct tcttcttcat cagtctacgt tcacacaatc tttcacccac ctattcaaag    180
ctctctccgg aagtttcgag gggttggttg ttggttttcc cgatgacttc ggatggagct    240
acgtcgacat cagcagctgc agctgcggcg gcggcagcag cggcgaggag gaagccgtcg    300
tggagagaaa gggagaataa tcggaggaga gaaagacgga gaagagctgt agctgcgaag    360
atatacactg gcttagagc tcaaggtgat tataatttgc ctaaacattg tgataataat      420
gaagtcctta aagctctttg tgttgaagct ggttgggttt ttgaagaaga tggtactact    480
tatcgcaagg gatgcaagcc tttacctggt gagatagctg ggacttcatc tcgagtaact    540
ccatattcat cacagaacca gagccctctt tcatcagcct ttcaaagtcc catcccatct    600
taccaagtta gcccgtcttc ttcatcattc ccgagtcctt ctcgcggtga accaaataac    660
aacatgtcct ctacattctt cccttcctc agaaatggtg gcattccttc ttctcttcct     720
tccctcagaa tctcaaacag ttgtccagtt accccaccgg tctcatcgcc gacttctaag    780
aacccgaaac cgttgcctaa ctgggaatct atcgctaagc aatccatggc cattgctaaa    840
caatcaatgg cgtcttttaa ttatcctttc tatgcggttt ctgcacctgc tagtccgaca    900
catcgccacc agtttcatac cctggctact ataccgaat gtgatgagtc tgactcttcc     960
actgttgatt ctggtcattg gataagcttt cagaagtttg cacaacaaca gccattctct   1020
gcctctatgg tgccaacctc tcctacctc aatcttgtga aacctgcgcc tcagcagatg    1080
tctccaaata ctgctgcctt ccaagagatt ggtcaaagct ctgagtttaa atttgagaat   1140
```

```
agccaagtta aaccctggga aggagagagg atacatgatg tgggtatgga ggatcttgag   1200
cttacacttg gaaatgggaa ggctcgtggt tgacataaac aactaggcaa acccaaatgg   1260
catgtcattg gaaatgagaa aactaatcct cttgagtatt ttcttcttcg tccaggtatt   1320
tggatcttta tggaatctca tatgttcttc acttattatc caaatatgct gcccaaagcc   1380
ttctccatgg aagcattgga gtgttagagt ggttattcaa ttcatgaatt tggtttcaaa   1440
agcattattt gtagat                                                  1456
```

<210> SEQ ID NO 6
<211> LENGTH: 336
<212> TYPE: PRT
<213> ORGANISM: ARABIDOPSIS THALIANA

<400> SEQUENCE: 6

```
Met Thr Ser Asp Gly Ala Thr Ser Ala Ala Ala Ala Ala
 1               5                  10              15

Ala Ala Ala Ala Arg Arg Lys Pro Ser Trp Arg Glu Arg Glu Asn
            20                  25                  30

Asn Arg Arg Arg Glu Arg Arg Arg Ala Val Ala Ala Lys Ile Tyr
        35                  40                  45

Thr Gly Leu Arg Ala Gln Gly Asp Tyr Asn Leu Pro Lys His Cys Asp
    50                  55                  60

Asn Asn Glu Val Leu Lys Ala Leu Cys Val Glu Ala Gly Trp Val Val
65                  70                  75                  80

Glu Glu Asp Gly Thr Thr Tyr Arg Lys Gly Cys Lys Pro Leu Pro Gly
                85                  90                  95

Glu Ile Ala Gly Thr Ser Ser Arg Val Thr Pro Tyr Ser Ser Gln Asn
            100                 105                 110

Gln Ser Pro Leu Ser Ser Ala Phe Gln Ser Pro Ile Pro Ser Tyr Gln
        115                 120                 125

Val Ser Pro Ser Ser Ser Phe Pro Ser Pro Ser Arg Gly Glu Pro
    130                 135                 140

Asn Asn Asn Met Ser Ser Thr Phe Phe Pro Phe Leu Arg Asn Gly Gly
145                 150                 155                 160

Ile Pro Ser Ser Leu Pro Ser Leu Arg Ile Ser Asn Ser Cys Pro Val
                165                 170                 175

Thr Pro Pro Val Ser Ser Pro Thr Ser Lys Asn Pro Lys Pro Leu Pro
            180                 185                 190

Asn Trp Glu Ser Ile Ala Lys Gln Ser Met Ala Ile Ala Lys Gln Ser
        195                 200                 205

Met Ala Ser Phe Asn Tyr Pro Phe Tyr Ala Val Ser Ala Pro Ala Ser
    210                 215                 220

Pro Thr His Arg His Gln Phe His Thr Pro Ala Thr Ile Pro Glu Cys
225                 230                 235                 240

Asp Glu Ser Asp Ser Ser Thr Val Asp Ser Gly His Trp Ile Ser Phe
                245                 250                 255

Gln Lys Phe Ala Gln Gln Gln Pro Phe Ser Ala Ser Met Val Pro Thr
            260                 265                 270

Ser Pro Thr Phe Asn Leu Val Lys Pro Ala Pro Gln Gln Met Ser Pro
        275                 280                 285

Asn Thr Ala Ala Phe Gln Glu Ile Gly Gln Ser Ser Glu Phe Lys Phe
    290                 295                 300

Glu Asn Ser Gln Val Lys Pro Trp Glu Gly Glu Arg Ile His Asp Val
```

```
                305                 310                 315                 320

Gly Met Glu Asp Leu Glu Leu Thr Leu Gly Asn Gly Lys Ala Arg Gly
                325                 330                 335

<210> SEQ ID NO 7
<211> LENGTH: 336
<212> TYPE: PRT
<213> ORGANISM: ARABIDOPSIS THALIANA

<400> SEQUENCE: 7

Met Thr Ser Asp Gly Ala Thr Ser Ala Ala Ala Ala Ala
  1               5                  10                  15

Ala Ala Ala Ala Arg Arg Lys Pro Ser Trp Arg Glu Arg Glu Asn
                 20                  25                  30

Asn Arg Arg Glu Arg Arg Arg Ala Val Ala Ala Lys Ile Tyr
             35                  40                  45

Thr Gly Leu Arg Ala Gln Gly Asp Tyr Asn Leu Pro Lys His Cys Asp
         50                  55                  60

Asn Asn Glu Val Leu Lys Ala Leu Cys Val Glu Ala Gly Trp Val Val
 65                  70                  75                  80

Glu Glu Asp Gly Thr Thr Tyr Arg Lys Gly Cys Lys Pro Leu Pro Gly
                 85                  90                  95

Glu Ile Ala Gly Thr Ser Ser Arg Val Thr Pro Tyr Ser Ser Gln Asn
            100                 105                 110

Gln Ser Pro Leu Ser Ser Ala Phe Gln Ser Pro Ile Pro Ser Tyr Gln
            115                 120                 125

Val Ser Pro Ser Ser Ser Phe Pro Ser Pro Ser Arg Gly Glu Pro
        130                 135                 140

Asn Asn Asn Met Ser Ser Thr Phe Phe Pro Phe Leu Arg Asn Gly Gly
145                 150                 155                 160

Ile Pro Ser Ser Leu Pro Ser Leu Arg Ile Ser Asn Ser Cys Pro Val
                165                 170                 175

Thr Pro Pro Val Ser Ser Pro Thr Ser Lys Asn Pro Lys Pro Leu Pro
            180                 185                 190

Asn Trp Glu Ser Ile Ala Lys Gln Ser Met Ala Ile Ala Lys Gln Ser
        195                 200                 205

Met Ala Ser Phe Asn Tyr Pro Phe Tyr Ala Val Ser Ala Pro Ala Ser
    210                 215                 220

Pro Thr His Arg His Gln Phe His Thr Leu Ala Thr Ile Pro Glu Cys
225                 230                 235                 240

Asp Glu Ser Asp Ser Ser Thr Val Asp Ser Gly His Trp Ile Ser Phe
                245                 250                 255

Gln Lys Phe Ala Gln Gln Pro Phe Ser Ala Ser Met Val Pro Thr
            260                 265                 270

Ser Pro Thr Phe Asn Leu Val Lys Pro Ala Pro Gln Gln Met Ser Pro
        275                 280                 285

Asn Thr Ala Ala Phe Gln Glu Ile Gly Gln Ser Ser Glu Phe Lys Phe
    290                 295                 300

Glu Asn Ser Gln Val Lys Pro Trp Glu Gly Glu Arg Ile His Asp Val
305                 310                 315                 320

Gly Met Glu Asp Leu Glu Leu Thr Leu Gly Asn Gly Lys Ala Arg Gly
                325                 330                 335

<210> SEQ ID NO 8
<211> LENGTH: 335
```

```
<212> TYPE: PRT
<213> ORGANISM: ARABIDOPSIS THALIANA

<400> SEQUENCE: 8

Met Thr Ser Asp Gly Ala Thr Ser Thr Ser Ala Ala Ala Ala Ala Ala
  1               5                  10                  15

Ala Met Ala Thr Arg Arg Lys Pro Ser Trp Arg Glu Arg Glu Asn Asn
             20                  25                  30

Arg Arg Arg Glu Arg Arg Arg Ala Val Ala Ala Lys Ile Tyr Thr
         35                  40                  45

Gly Leu Arg Ala Gln Gly Asn Tyr Asn Leu Pro Lys His Cys Asp Asn
 50                  55                  60

Asn Glu Val Leu Lys Ala Leu Cys Ser Glu Ala Gly Trp Val Val Glu
 65                  70                  75                  80

Glu Asp Gly Thr Thr Tyr Arg Lys Gly His Lys Pro Leu Pro Gly Asp
                 85                  90                  95

Met Ala Gly Ser Ser Ser Arg Ala Thr Pro Tyr Ser Ser His Asn Gln
            100                 105                 110

Ser Pro Leu Ser Ser Thr Phe Asp Ser Pro Ile Leu Ser Tyr Gln Val
        115                 120                 125

Ser Pro Ser Ser Ser Ser Phe Pro Ser Pro Ser Arg Val Gly Asp Pro
    130                 135                 140

His Asn Ile Ser Thr Ile Phe Pro Phe Leu Arg Asn Gly Gly Ile Pro
145                 150                 155                 160

Ser Ser Leu Pro Pro Leu Arg Ile Ser Asn Ser Ala Pro Val Thr Pro
                165                 170                 175

Pro Val Ser Ser Pro Thr Ser Arg Asn Pro Lys Pro Leu Pro Thr Trp
            180                 185                 190

Glu Ser Phe Thr Lys Gln Ser Met Ser Met Ala Ala Lys Gln Ser Met
        195                 200                 205

Thr Ser Leu Asn Tyr Pro Phe Tyr Ala Val Ser Ala Pro Ala Ser Pro
    210                 215                 220

Thr His His Arg Gln Phe His Ala Pro Ala Thr Ile Pro Glu Cys Asp
225                 230                 235                 240

Glu Ser Asp Ser Ser Thr Val Asp Ser Gly His Trp Ile Ser Phe Gln
                245                 250                 255

Lys Phe Ala Gln Gln Pro Phe Ser Ala Ser Met Val Pro Thr Ser
            260                 265                 270

Pro Thr Phe Asn Leu Val Lys Pro Ala Pro Gln Leu Ser Pro Asn
        275                 280                 285

Thr Ala Ala Ile Gln Glu Ile Gly Gln Ser Ser Glu Phe Lys Phe Glu
    290                 295                 300

Asn Ser Gln Val Lys Pro Trp Glu Gly Glu Arg Ile His Asp Val Ala
305                 310                 315                 320

Met Glu Asp Leu Glu Leu Thr Leu Gly Asn Gly Lys Ala His Ser
                325                 330                 335

<210> SEQ ID NO 9
<211> LENGTH: 3000
<212> TYPE: DNA
<213> ORGANISM: ARABIDOPSIS THALIANA

<400> SEQUENCE: 9
tgaatatcct cacatttcca ttttcgactc tctttagtaa attttgaagt agtagaatga      60
tgtagaatgt tttgttttat caatcacaca gttttgtgaa atcacgattt ccatccacta     120
```

-continued

```
ttcaagaaaa acatcaagtg gaagaaataa taaaccaaaa ccatcgcaac aaaatgcata      180
tcacgagtat agaatgaaca actacactg tcaaatactt aatttaggac ttaaacttcg       240
ctttcagaca acttggttcg gaaacttgac catccgtcat gttgatatac acaatccatc     300
tcaaatgtag tagtgaatca ctatatcagc atgtgttatc aaacgcaagt tgtcactaag     360
atcggagctt ctagttcaaa atgttgataa gtattacgaa agtacaattg aatataccaa     420
ttatacatcc aaacacgtcc atgcttctcc actcgagttc tctttggaaa tctatataat     480
ccgtcggttt ggtatttttac tagttgtacg tagtgtctcc cctcatatgt attgagtctt    540
tatagtttgt tgcctcgtat acgatagaaa gtaaaggcta aaaaaccata ctatttcata    600
aagggtttat ttagttaact tttaatctaa accatgtatc actccatttt acgtatattc    660
gttttcacaa ataatctact aaataatttt gtaatgtgat aaaattaaag aataaacaca    720
tgatacataa acagtcagga caaaagtaag cactcatttt cttctattca tactatagtg    780
aaacactatt ttatttttat ccatatacta tagtgacaaa ttaatctaat cattaaatgt    840
tatgaggctc aaaacaattt gttttcttat ttaacatggc cgatcccctc ataaaccaat    900
cagatggtgt gttttccggt catactcgtg taggacccac ttcattacaa tggccccaca    960
tgtctctcta tctttttctc ctctttataa aatcagctcc ttttcttaca cagatttaga  1020
gaaacacaac ataaaacgta cttcttcttc aaaacgcgaa accacactgt aagttacgta  1080
caccaccacc tatcctcacc attcatcatc gacacgtggc tggtttaact caaatcaacg  1140
gtgaattctt tttgctttt tatttaaat aatgaatgaa aagattcttc tataattcca    1200
gcgaagaaga aagaaaaaaa aaagcgtatt cctcgtgagc actaacttct cactcattct  1260
tcttcttcag ctgaatccaa atacccattt ccatttttaa ccgtggttgg attgttttga  1320
gagttgaagg aagaagatga cgtctgacgg agcaacgtcg acgtcagctg cagctgcagc  1380
agcagcgatg gcgacgagga ggaaaccgtc gtggagagag agggagaaca atcggagaag  1440
agagcggcgg agaagagctg ttgcggcgaa gatttatact ggtcttagag ctcaaggtaa  1500
ctacaatctt ccaaaacatt gtgacaacaa tgaggttctt aaggctcttt gttctgaagc  1560
tggttgggtt gttgaagaag acggaactac ttatcgcaag gtcagtatca aacgcatttt  1620
tacttagatc tgatgttatc tgatgattta gctgttgaat ctgaagattt ggatttgaaa  1680
ttggtcaaat tgggattttc ttggctatga attcgaggtt tttagctgag gaagctcagt  1740
tttattctaa aattggatcg agattccttg cggagaaagt gacctttagg gttcttctta  1800
ctaatttgag aaccgaatta gctttacttt cacttggtta ctatatttag atctctcctt  1860
tagcttttga ttgattgtga cattgtgatg tttttggtat tgttctatga gcaacaggga  1920
cacaagcctc tacctggtga catggctgga tcatcttctc gagcaactcc ttactcttcc  1980
cataaccaaa gtcctctttc ttccactttt gatagcccca tcttatctta ccaagtcagt  2040
ccttcctctt cttcattccc gagtccttct cgagttggtg atccacacaa tatctccaca  2100
atcttccctt tcctcaggaa tggtggtatt ccttcatcgc ttcctccact tagaatctca  2160
aacagtgctc ctgtcactcc accagtgtca tccccaactt ctagaaaccc caaaccattg  2220
cctacttggg aatcttttac caaacaatcc atgtccatgg ctgctaaaca gtcaatgact  2280 tcttttgaact accgttttta tgcggtgtct gcacctgcca gtcctactca tcatcgccag  2340
ttccatgctc tggctactat acctgaatgt gatgagtctg actcttccac tgttgattct  2400
ggtcattgga taagctttca aaagtttgca caacaacagc cattctctgc ctctatggtg  2460
```

```
ccaacctcgc ctaccttcaa tctcgtgaaa cctgcaccac agcaattgtc tccaaacaca    2520
gcagcaatcc aagagattgg tcaaagctcc gagtttaagt ttgagaacag ccaagttaag    2580
ccatgggaag gggagaggat ccatgatgtg gctatggagg atctagagct cacgcttgga    2640
aatggtaaag ctcatagttg agatgaagta tacatgaacc tgttatgtca tgtcggaagg    2700
aaggattgga gaatgagaat tagtgtgttg ttcattcagt tcatggtttt ggttcttgtt    2760
ctagaatcga tattcattgt accagtgagt ttgtttcaca acgcattatt tgtagataga    2820
atgtttaaga tgtatgtttc tattatcatt ccttttaggt cttgaaaaca ttacaaatat    2880
attacatgat aagtggcttt gaaatgtaaa ttatatatcg gatgatgaaa cagagaaaaa    2940
caagtgaggc taaaacaaag acttgggatg taataacaag atcagagagg ttaagaaaga    3000
```

<210> SEQ ID NO 10
<211> LENGTH: 335
<212> TYPE: PRT
<213> ORGANISM: ARABIDOPSIS THALIANA

<400> SEQUENCE: 10

```
Met Thr Ser Asp Gly Ala Thr Ser Thr Ala Ala Ala Ala Ala Ala Ala
 1               5                  10                  15

Ala Met Ala Thr Arg Arg Lys Pro Ser Trp Arg Glu Arg Glu Asn Asn
            20                  25                  30

Arg Arg Arg Glu Arg Arg Arg Ala Val Ala Ala Lys Ile Tyr Thr
        35                  40                  45

Gly Leu Arg Ala Gln Gly Asn Tyr Asn Leu Pro Lys His Cys Asp Asn
    50                  55                  60

Asn Glu Val Leu Lys Ala Leu Cys Ser Glu Ala Gly Trp Val Val Glu
65                  70                  75                  80

Glu Asp Gly Thr Thr Tyr Arg Lys Gly His Lys Pro Leu Pro Gly Asp
                85                  90                  95

Met Ala Gly Ser Ser Arg Ala Thr Pro Tyr Ser Ser His Asn Gln
            100                 105                 110

Ser Pro Leu Ser Ser Thr Phe Asp Ser Pro Ile Leu Ser Tyr Gln Val
        115                 120                 125

Ser Pro Ser Ser Ser Ser Phe Pro Ser Pro Ser Arg Val Gly Asp Pro
    130                 135                 140

His Asn Ile Ser Thr Ile Phe Pro Phe Leu Arg Asn Gly Gly Ile Pro
145                 150                 155                 160

Ser Ser Leu Pro Pro Leu Arg Ile Ser Asn Ser Ala Pro Val Thr Pro
                165                 170                 175

Pro Val Ser Ser Pro Thr Ser Arg Asn Pro Lys Pro Leu Pro Thr Trp
            180                 185                 190

Glu Ser Phe Thr Lys Gln Ser Met Ser Met Ala Ala Lys Gln Ser Met
        195                 200                 205

Thr Ser Leu Asn Tyr Pro Phe Tyr Ala Val Ser Ala Pro Ala Ser Pro
    210                 215                 220

Thr His His Arg Gln Phe His Ala Leu Ala Thr Ile Pro Glu Cys Asp
225                 230                 235                 240

Glu Ser Asp Ser Ser Thr Val Asp Ser Gly His Trp Ile Ser Phe Gln
                245                 250                 255

Lys Phe Ala Gln Gln Gln Pro Phe Ser Ala Ser Met Val Pro Thr Ser
            260                 265                 270

Pro Thr Phe Asn Leu Val Lys Pro Ala Pro Gln Gln Leu Ser Pro Asn
        275                 280                 285
```

```
Thr Ala Ala Ile Gln Glu Ile Gly Gln Ser Ser Glu Phe Lys Phe Glu
        290                 295                 300

Asn Ser Gln Val Lys Pro Trp Glu Gly Glu Arg Ile His Asp Val Ala
305                 310                 315                 320

Met Glu Asp Leu Glu Leu Thr Leu Gly Asn Gly Lys Ala His Ser
                325                 330                 335

<210> SEQ ID NO 11
<211> LENGTH: 1213
<212> TYPE: DNA
<213> ORGANISM: ARABIDOPSIS THALIANA

<400> SEQUENCE: 11
tataattcca gcgaagaaga aagaaaaaaa aaagcgtatt cctcgtgagc actaacttct      60
cactcattct tcttcttcag ctgaatccaa atacccattt ccatttttaa ccgtggttgg     120
attgttttga gagttgaagg aagaagatga cgtctgacgg agcaacgtcg acgtcagctg     180
cagctgcagc agcagcgatg gcgacgagga ggaaaccgtc gtggagagag agggagaaca     240
atcggagaag agagcggcgg agaagagctg ttgcggcgaa gatttatact ggtcttagag     300
ctcaaggtaa ctacaatctt ccaaaacatt gtgacaacaa tgaggttctt aaggctcttt     360
gttctgaagc tggttgggtt gttgaagaag acggaactac ttatcgcaag ggacacaagc     420
ctctacctgg tgacatggct ggatcatctt ctcgagcaac tccttactct tcccataacc     480
aaagtcctct tcttccact tttgatagcc catcttatc ttaccaagtc agtccttcct     540
cttcttcatt cccgagtcct tctcgagttg gtgatccaca caatatctcc acaatcttcc     600
cttcctcag gaatggtggt attccttcat cgcttcctcc acttagaatc tcaaacagtg     660
ctcctgtcac tccaccagtg tcatccccaa cttctagaaa ccccaaacca ttgcctactt     720
gggaatcttt taccaaacaa tccatgtcca tggctgctaa acagtcaatg acttcttga     780
actaccgtt ttatgcggtg tctgcacctg ccagtcctac tcatcatcgc cagttccatg     840
ctccggctac tatacctgaa tgtgatgagt ctgactcttc cactgttgat tctggtcatt     900
ggataagctt tcaaaagttt gcacaacaac agccattctc tgcctctatg gtgccaacct     960
cgcctacctt caatctcgtg aaacctgcac cacagcaatt gtctccaaac acagcagcaa    1020
tccaagagat tggtcaaagc tccgagttta gtttgagaa cagccaagtt aagccatggg    1080
aaggggagag gatccatgat gtggctatgg aggatctaga gctcacgctt ggaaatggta    1140
aagctcatag ttgagatgaa gtatacatga acctgttatg tcatgtcgga aggaaggatt    1200
ggagaatgag aat                                                      1213

<210> SEQ ID NO 12
<211> LENGTH: 1213
<212> TYPE: DNA
<213> ORGANISM: ARABIDOPSIS THALIANA

<400> SEQUENCE: 12
tataattcca gcgaagaaga aagaaaaaaa aaagcgtatt cctcgtgagc actaacttct      60
cactcattct tcttcttcag ctgaatccaa atacccattt ccatttttaa ccgtggttgg     120
attgttttga gagttgaagg aagaagatga cgtctgacgg agcaacgtcg acgtcagctg     180
cagctgcagc agcagcgatg gcgacgagga ggaaaccgtc gtggagagag agggagaaca     240
atcggagaag agagcggcgg agaagagctg ttgcggcgaa gatttatact ggtcttagag     300
ctcaaggtaa ctacaatctt ccaaaacatt gtgacaacaa tgaggttctt aaggctcttt     360
```

```
gttctgaagc tggttgggtt gttgaagaag acggaactac ttatcgcaag ggacacaagc        420
ctctacctgg tgacatggct ggatcatctt ctcgagcaac tccttactct tcccataacc        480
aaagtcctct ttcttccact tttgatagcc ccatcttatc ttaccaagtc agtccttcct        540
cttcttcatt cccgagtcct tctcgagttg gtgatccaca caatatctcc acaatcttcc        600
ctttcctcag gaatggtggt attccttcat cgcttcctcc acttagaatc tcaaacagtg        660
ctcctgtcac tccaccagtg tcatccccaa cttctagaaa ccccaaacca ttgcctactt        720
gggaatcttt taccaaacaa tccatgtcca tggctgctaa acagtcaatg acttctttga        780
actacccgtt ttatgcggtg tctgcacctg ccagtcctac tcatcatcgc cagttccatg        840
ctctggctac tatacctgaa tgtgatgagt ctgactcttc cactgttgat tctggtcatt        900
ggataagctt tcaaaagttt gcacaacaac agccattctc tgcctctatg gtgccaacct        960
cgcctacctt caatctcgtg aaacctgcac cacagcaatt gtctccaaac acagcagcaa       1020
tccaagagat tggtcaaagc tccgagttta agtttgagaa cagccaagtt aagccatggg       1080
aaggggagag gatccatgat gtggctatgg aggatctaga gctcacgctt ggaaatggta       1140
aagctcatag ttgagatgaa gtatacatga acctgttatg tcatgtcgga aggaaggatt       1200
ggagaatgag aat                                                          1213
```

<210> SEQ ID NO 13
<211> LENGTH: 23
<212> TYPE: DNA
<213> ORGANISM: ARABIDOPSIS THALIANA

<400> SEQUENCE: 13

```
tctggtaccc acctattcaa agc                                                 23
```

<210> SEQ ID NO 14
<211> LENGTH: 27
<212> TYPE: DNA
<213> ORGANISM: ARABIDOPSIS THALIANA

<400> SEQUENCE: 14

```
tgaggatcca ctctaacact cccaatg                                             27
```

GENES INVOLVED IN BRASSINOSTEROID HORMONE ACTION IN PLANTS

GOVERNMENT RIGHTS

This invention was made with government support under U.S. Department of Agriculture (USDA) grant #99-35301-7903. The government may have certain rights in the invention.

BACKGROUND OF THE INVENTION

1. Field of the Invention

The present invention relates to the field of plant biology and specifically to methods of modifying brassinosteroid response pathways and plant growth. An *Arabidopsis* gene called BZR1, variants, homologs and mutants thereof, appear to be involved in brassinosteroid responses. Expression of the BZR1 gene or the dominant mutant known as bzr1-D result in a variety of useful phenotypes such as increased cell expansion, plant size, yield, and cell size.

2. Description of the Related Art

The brassinosteroids are a unique class of biologically active natural products that possess plant steroidal hormone activity. Brassinosteroids play important roles in multiple plant developmental processes, and are primarily required for normal cell elongation and expansion. In light-grown plants, brassinosteroid deficiency results in dwarfism, while in dark-grown plants, brassinosteroid deficiency confers characteristics of light-grown plants.

Most multicellular organisms use steroids as signaling molecules for physiological and developmental regulation. Two different modes of steroid actions have been described in animal systems: the well-studied gene regulation response mediated by nuclear receptors, and the rapid non-genomic responses mediated by proposed membrane-bound receptors (Beato, et al., *Cell* 83:851, 1995; Mangelsdorf, et al., *Cell* 83:835, 1995; Wehling, *Annu. Rev. Physiol.* 59:365, 1997; and Schmidt, et al., *Front Neuroendocrinol* 21:57, 2000).

In both plants and animals, hormones typically act by binding to specific receptor proteins, thereby creating a ligand/receptor complex. The binding of the hormone to the receptor is believed to initiate an allosteric alteration of the receptor protein. In some instances, such as steroid receptors in animal systems, the ligand/receptor complex is capable of binding with high affinity to certain specific sites on DNA to modulate gene expression. The ligand/receptor complex may also act elsewhere in the cell. Recent evidence indicates that in addition to intracellular, genomic effects, steroids also exhibit non-genomic effects, ie., they affect the surface of cells and alter ion permeability, as well as release of neurohormones and neurotransmitters. Steroids such as estrogens and adrenal steroids and their naturally produced and synthetic analogs have shown membrane effects. In view of the foregoing, it appears that steroids may cause synergistic interactions between non-genomic and genomic responses resulting in multiple developmental and morphological alterations.

Brassinolide, one of the major brassinosteroids, was first isolated from the pollen of rape (*Brassica napus*) (Grove, et al., *Nature*, 281:216 1979), and was found to be a novel plant growth-promoting factor. To date, about 40 brassinosteroids have been found. Brassinosteroids are present at very low concentrations, and have been found to occur in all plant species examined (for review, see Mandava, et al., *Ann. Rev. Plant Physiol. Plant Mol. Biol.* 39:23, 1988).

Several mutations have been found to affect either light-dependent or hormone signaling pathways, resulting in plants with a dwarf phenotype. Brassinosteroid application can rescue some types of dwarf mutants in *Arabidopsis* since these mutants have been found to be defective in some aspect of brassinosteroid biosynthesis. Recent advances in our understanding of both brassinosteroid biosynthesis pathways and brassinosteroid response pathways have involved a combination of both mutational and biochemical analysis.

Several mutations in brassinosteroid biosynthetic pathways have been found. The *Arabidopsis* dwf7 mutant blocks biosynthesis of 5-dehydroepisterol from episterol, while the mutant dwf5 blocks 24-methylenecholesterol biosynthesis from 5-dehydroepisterol. The mutants dim, dwf1, and lkb block synthesis of campesterol from 24-methylenecholesterol. The synthesis of 5 α-campestanol from campesterol is blocked in the det2 mutant of *Arabidopsis*. The DET2 gene encodes a steroid 5 α-reductase. Overexpression of the DET2 protein increases brassinolide levels and results in larger, more robust plants. Later steps in the brassinosteroid biosynthetic pathway are blocked in the mutants dwf4 and cpd. Both the CPD and DWF4 genes have been found to encode cytochrome P450 proteins.

While many proteins have been found to participate in the biosynthesis of brassinosteroids, other proteins are involved in the coordination of plant responses to the presence of brassinolide or other brassinosteroids. Mutants in brassinosteroid perception are useful to study this aspect of brassinolide pathways, as several mutants have now been found which are blocked at some point in the brassinolide perception process. For example, bri1, cbb2, bin1, dwf2, lka, and cu-3 are thought to be blocked at some point between brassinolide synthesis and brassinosteroid-regulated responses.

Several of these mutants have been found to contain lesions in the Brassinosteroid-insensitive 1 (BRI1) gene. The BRI1 protein is a leucine-rich repeat receptor serine/threonine kinase, (Friedrichsen, et al., *Plant Physiol.* 123: 1247, 2000) containing a transmembrane region and an extracellular domain that functions as a plant brassinosteroid receptor at the plasma membrane surface (Wang, et al., *Nature* 410: 380, 2001; He et al., *Science* 288: 2360, 2000). BRI1 apparently becomes autophosphorylated upon exogenous application of brassinolide. Together, these findings suggest that the BRI1 protein is a brassinolide receptor kinase that transduces steroid signals across the plasma membrane (Wang, et al., *Nature* 410:380, 2001).

On a cellular level, brassinosteroids produce a variety of phenotypic changes in plants. For example, brassinosteroids accelerate seed germination and growth of seedlings, increase cell size and elongation, alter the arrangement of cortical microtubules and cellulose microfilaments, promote differentiation of xylem, promote leaf enlargement, increase plant dry weight, increase plant yield, induce H+ export and membrane hyperpolarization, promote tissue senescence in the dark, repress anthocyanin production in light-grown plants, and induce plant pathogen resistance responses to numerous bacterial and fungal species.

It is clear from the above discussion that brassinosteroids are an important group of plant modulatory molecules that play a role in many aspects of plant growth. Information leading to the further elucidation of brassinosteroid biosynthesis pathways and brassinosteroid response pathways is likely to be of agronomic importance. However, not all of the brassinosteroid pathway genes have been discovered. Thus what is needed in the art is a more complete description of brassinosteroid response pathway genes.

SUMMARY OF THE INVENTION

One embodiment of the present invention provides a method of producing a genetically modified plant having increased size as compared to a wild-type plant, by contacting a plant cell with at least one nucleic acid sequence encoding a BZR1 protein, the nucleic acid sequence operably associated with a promoter, to obtain a transformed plant cell, producing a plant from said transformed plant cell, and then selecting a plant exhibiting an increased size.

Another embodiment of the present invention provides a genetically modified plant exhibiting increased size in comparison to a wild-type plant, wherein the genetically modified plant includes at least one exogenous nucleic acid sequence encoding a BZR1 polypeptide, wherein the polypeptide comprises an amino acid sequence with at least 80% sequence homology to SEQ ID NO:6.

Yet another embodiment of the present invention provides a genetically modified seed which produces a plant exhibiting increased size in comparison to a wild-type plant, wherein the genetically modified seed includes at least one exogenous nucleic acid sequence encoding a BZR1 polypeptide, wherein the polypeptide includes an amino acid sequence with at least 80% sequence homology to SEQ ID NO:6.

In another embodiment of the present invention, a substantially purified bzr1-D polypeptide having the amino acid sequence of SEQ ID NO: 7 is provided.

Another embodiment of the present invention provides a nucleic acid having a nucleotide sequence encoding a bzr1-D polypeptide having the amino acid sequence of SEQ ID NO: 7.

DETAILED DESCRIPTION

Embodiments of the invention include nucleic acid molecules encoding the BRASSINAZOLE RESISTANT 1 (BZR1) polypeptide and variants thereof, including the protein product of the dominant mutant bzr1-D known as bzr1-D, all of which are involved in the regulation of cell expansion in plants through effects on brassinosteroid response pathways. The BZR1 protein and bzr1-D protein appear to act downstream of the brassinosteroid receptor, so it is involved in the brassinosteroid response pathway rather than the brassinosteriod biosynthetic pathway. Embodiments of the invention include methods of modulating brassinosteriod-related responses, methods of modulating signaling pathways, methods of identifying compounds involved in signaling pathways, and methods of altering plant phenotypes by altering the genes encoding BZR1 polypeptides is described.

The present invention thus provides both an isolated gene, BZR1, (SEQ ID NO: 1), and an altered gene, bzr1-D (SEQ ID NO: 2), both of which are involved in brassinosteroid-related responses. The present invention is additionally based on the discovery that overexpression of the mutant bzr1-D gene (SEQ ID NO: 2) resulted in multiple phenotypic changes, including an elongation of the hypocotyl, radial expansion of the leaf blade, an increase in leaf size, increased petiole length, and alterations in the degree of greening. In another embodiment, the present invention provides another gene, BZR2, (SEQ ID NO: 3), which is similar to BZR1 and is also involved in brassinosteroid-related responses. Alterations of the BZR2 gene such as the dominant mutation bzr2-D are additionally provided by the present invention.

The bzr1-D mutant phenotype, containing an alteration in the brassinosteroid response pathway, was identified using a plant growth inhibitor-based screening procedure. Plant growth inhibitors are useful to identify components of plant hormone pathways. The triazole brassinazole specifically inhibits brassinosteroid biosynthesis. When used as part of a screening procedure, brassinazole treatment can be used to assist in the identification of brassinosteroid pathway components. Plants with a tall phenotype among the plants chemically dwarfed by brassinazole treatment can be selected for further analysis. Brassinazole-insensitive, tall plants are considered likely to contain mutations in some aspect of BR-related synthesis or signaling pathways.

EMS mutagenized *Arabidopsis* seeds were grown into plants that were then subjected to a suppressor screen for mutants insensitive to the brassinosteroid pathway inhibitor brassinazole. While most of the mutagenized plants became stunted when treated with brassinazole, one plant exhibited a taller phenotype, similar to that of untreated plants. Sequence analysis of plants with this brassinazole-insensitive phenotype showed a C to T missense mutation in the BZR1 gene. This mutation (herein referred to as bzr1-D) resulted in a proline to leucine substitution at amino acid position 234 in the carboxyl-terminal half of the protein. Interestingly, this substitution mutation results in an activated form of the protein, rather than a non-functional form. The mutant protein is herein referred to as bzr1-D (SEQ ID NO. 7).

The bzr1-D mutant was crossed into either the brassinosteroid biosynthetic mutant det2 or the brassinosteroid insensitive mutant bri1 background. The double mutants created from these crosses exhibit phenotypes similar to that of bzr1-D mutant plants. The bzr1-D mutation suppresses all of the phenotypes of both the brassinosteroid biosynthetic mutant and the brassinosteroid receptor mutant. These results demonstrate that BZR1 functions downstream of the BRI1 receptor in the brassinosteroid signaling pathway.

Several *Arabidopsis* genes homologous to BZR1 were identified by a BLAST-based nucleic acid database search. The *Arabidopsis* gene that shares the highest homology with BZR1 is named BZR2 (gi/8778414 and gi/665069 and gi/15222005), which shares 88% identity and 90% similarity with BZR1 in amino acid sequence.

Accordingly, in another embodiment, the present invention provides an isolated gene, BZR2, (SEQ ID NO: 3), which is also expected to be involved in brassinosteroid-related responses. BZR2 (SEQ ID NO: 8) has now been shown to have the same function and activity as BZR1 (SEQ ID NO: 6). Mutations that suppress the dwarf phenotype of a bri1 mutant were identified. One of the bri1 suppressor mutants named bes1 showed very similar phenotypes as the bzr1-D/bri1 double mutant. By sequencing the BZR1 and BZR2 genes of the bes1 mutant, we determined that bes1 contains a mutation in the BZR2 gene. The mutation in this gene (herein referred to as bzr2-D), (SEQ ID NO: 9) resulted in a proline to leucine substitution at amino acid position 233 of BZR2, resulting in the mutant protein sequence bzr2-D (SEQ ID NO: 10) which corresponds to the same amino acid change in bzr1-D. These results demonstrate that BZR2 has the same function as BZR1 in brassinosteroid regulation of plant development, and that the same mutations in bzr1-D and bzr2-D cause similar developmental phenotypes. Both bzr1-D (SEQ ID NO: 7) and bzr2-D (SEQ ID NO: 10) mutant proteins are more active and are more efficient in generating cell elongation phenotypes than their wild type forms. Expression of bzr2-D mutant genes in transgenic plants causes similar phenotypes of increased cell elongation and growth as caused by expression of the bzr1-D mutant gene.

Plants with altered responses to brassinosteroids may be of particular economic importance to agriculture. For example, modification of brassinosteroid response pathways may produce larger plants with higher crop yields. Additionally, these response pathways may be modified in specific tissues or at specific developmental stages, to increase desirable qualities in agricultural products. It may be possible to produce crops with increased fruit size by linking fruit-specific promoters to genes with modified brassinosteroid responses. Embodiments of the present invention include plants having modified expression of BZR1, or plants expressing bzr1-D, where the plants show altered responses to brassinosteroids.

BZR1 Polypeptides

In a first embodiment, the present invention provides a substantially pure BZR1 polypeptide (SEQ ID NO: 6). BZR1 polypeptide is exemplified by the amino acid sequence shown in SEQ ID NO: 6. BZR1 is further exemplified by its function in the brassinosteroid response pathway.

The term "substantially pure" as used herein refers to BZR1 polypeptide that is substantially free of other proteins, lipids, carbohydrates or other materials with which it is naturally associated. One skilled in the art can purify BZR1 using standard techniques for protein purification. The purity of the BZR1 polypeptide can also be determined by amino-terminal amino acid sequence analysis.

The invention includes functional BZR1 polypeptides and functional fragments thereof, as well as mutants and variants having the same biological function or activity. As used herein, the terms "functional fragment", "mutant" and "variant" refers to a polypeptide which possesses biological function or activity identified through a defined functional assay and associated with a particular biologic, morphologic, or phenotypic alteration in the cell. The term "functional fragments of BZR1 polypeptide", refers to all fragments of BZR1 (SEQ ID NO: 6) that retain BZR1 activity and function in the brassinolide response pathway. Functional fragments, for example, can vary in size from a polypeptide fragment as small as an epitope capable of binding an antibody molecule, to a large polypeptide capable of participating in the characteristic induction or programming of phenotypic changes within a cell. Furthermore, the function or activity of BZR1 in the brassinosteroid response pathway can be utilized in bioassays to identify functional fragments of BZR1 polypeptide or related polypeptides.

Modifications of the BZR1 primary amino acid sequence may result in mutant or variant proteins having substantially equivalent activity to the BZR1 polypeptide described herein SEQ ID NO: 6. Such modifications may be deliberate, as by site-directed mutagenesis, or may occur by spontaneous changes in amino acid sequences where these changes produce modified polypeptides having substantially equivalent activity to the BZR1 polypeptide.

The present invention additionally provides a substantially pure altered polypeptide bzr1-D. bzr1-D polypeptide is exemplified by the amino acid sequence shown SEQ ID NO: 7. As described above, the altered bzr1-D protein was prepared by carrying out a chemical mutagenesis procedure on *Arabidopsis thaliana* plants, followed by a brassinazole screening procedure to look for plants with a brassinazole-insensitive phenotype. In comparison to the BZR1 protein, the bzr1-D polypeptide contains a sequence modification from proline to leucine at amino acid 234.

Any polypeptides produced by minor modifications of the BZR1 primary amino acid sequence are included herein as long as the biological activity of BZR1 is present; e.g., having a role in brassinosteroid response pathways leading to increased plant size or plant yield.

As used herein, the term "yield" or "plant yield" refers to increased plant growth, increased crop growth, and/or increased biomass production. Further, deletion of one or more amino acids can also result in a modification of the structure of the resultant molecule without significantly altering its activity. This can lead to the development of a smaller active molecule which could have broader utility.

Polypeptides of the present invention include amino acid sequences substantially the same as the sequence of BZR1 set forth in SEQ ID NO: 6. The term "substantially the same" refers to amino acid sequences that retain the activity of BZR1 as described herein. The polypeptides of the invention include conservative variations of the BZR1 polypeptide sequence. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

Proteins of the invention can be analyzed by standard SDS-PAGE and/or immunoprecipitation analysis and/or Western blot analysis, for example. In addition, the in vitro synthesized (IVS) protein assay as described in the present examples can be used to analyze BZR1 protein product.

Another aspect of the invention is polypeptides or fragments thereof which have at least about 70%, at least about 80%, at least about 85%, at least about 90%, at least about 95%, or more than about 95% homology to one of the polypeptides of SEQ ID NO: 6, and sequences substantially identical thereto, or a fragment comprising at least 5, 10, 15, 20, 25, 30, 35, 40, 50, 75, 100, 150, 200, 250, or 300 consecutive amino acids thereof. Homology may be determined using any of the methods described herein which align the polypeptides or fragments being compared and determines the extent of amino acid identity or similarity between them. It will be appreciated that amino acid "homology" includes conservative amino acid substitutions such as those described above.

The polypeptides or fragments having homology to one of the polypeptides of SEQ ID NO: 6, and sequences substantially identical thereto, or a fragment comprising at least about 5, 10, 15, 20, 25, 30, 35, 40, 50, 75, 100, 150, 200, 250, or 300 consecutive amino acids thereof may be obtained by isolating the nucleic acids encoding them using the techniques described herein Alternatively, the homologous polypeptides or fragments may be obtained through biochemical enrichment or purification procedures. The sequence of potentially homologous polypeptides or fragments may be determined by proteolytic digestion, gel electrophoresis and/or microsequencing. The sequence of the prospective homologous polypeptide or fragment can be compared to one of the polypeptides of SEQ ID NO: 6, and sequences substantially identical thereto, or a fragment comprising at least about 5, 10, 15, 20, 25, 30, 35, 40, 50, 75, 100, 150, 200, 250, or 300 consecutive amino acids thereof using any of the programs described above.

Accordingly, polypeptides of the present invention include BZR2 (SEQ ID NO: 8), a polypeptide with considerable homology to BZR1. As mentioned earlier, the BZR2 gene (SEQ ID NO: 3) and its dominant mutant bzr2-D (SEQ ID NO: 9) confer similar phenotypes and function as BZR1 and bzr1-D, respectively.

Homologous amino acid or nucleotide sequences preferably comprise enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Basic Local Aligument Search Tool) (for a review ses Ailsohul, et at, Meth Enzymol. 266:460, 1996; and Altschul, et al., Nature Genet. 6:119, 1994). BLAST is the heuristic search algorithm employed by the programs blastp, blastn, blastx, tblastn, and tblastx using the statistical methods of Karlin and Altschul (available on the world wide web at ncbi.nih.gov/BLAST/; Altschul, et al., J. Mol. Biol. 215:403, 1990). The BLAST programs were tailored for sequence similarity searching, for example to identify homologues to a query sequence. The BLAST pages offer several different databases for searching. Some of these, like ecoli, dbEST and month, are subsets of the NCBI (National Center for Biotechnology Information) databases. Others, such as SwiasProt, PDB and Kabat arc complied outside of NCBI. Protein BLAST allows one to input protein sequences and compare these against other protein sequences.

The five BLAST programs available on the world wide web at ncbi.nlm.nih.gov perform the following tasks:

blastp—compares an amino acid query sequence against a protein sequence database.

blastn—compares a nucleotide query sequence against a nucleotide sequence database.

blastx—compares the six-frame conceptual translation products of a nucleotide query sequence (both strands) against a protein sequence database.

tblastn—compares a protein query sequence against a nucleotide sequence database dynamically translated in all six reading frames (both strands).

tblastx—compares the six-frame translations of a nucleotide query sequence against the six-frame translations of a nucleotide sequence database.

A blastn 2.2.2 (Apr. 13, 2001) search was performed using the BZR1 genomic sequence (SEQ ID NO: 1) as the query sequence. The nearest sequence is a 100% identity match (1975/1975). The matching sequence is *Arabidopsis thaliana* chromosome 1 BAC F9E10 genomic sequence (GI/12323880:c17658-17392, c17038-16304), locus: AC013258, 1002 bp Accession AC013258; version: AC013258.5; Lin et al, submitted Nov. 5, 1999, and updated on Jan. 19, 2001.

A search for homologous proteins was performed using the BLASTP version 2.2.1 program and the BZR1 amino acid sequence (SEQ ID NO: 6) as the query sequence. A pairwise comparison between BZR1 amino acid sequence and the most similar proteins was performed using the BLASTP comparison tool with the following settings: matrix: blosum 62, gap open: 11, gap extension: 1, dropoff: 50, expect: 10 wordsize: 3, and filter: off. By "percentage identity" is meant % of identical amino acids between the two compared proteins. By "% similarity" is meant the percentage of similar amino acids between the two compared proteins.

One putative protein sequence was found to be identical to the BZR1 sequence: gi/12323903: an unknown protein from BAC clone F9E10, derived from chromosome 1 of *Arabidopsis thaliana*, submitted by Lin, et al., on Nov. 5, 1999; and Town et al., on Jan. 19, 2001. Pairwise comparison with BZR1: 100% identity to BZR1 (333/333).

A pairwise comparison between the BZR1 protein sequence and the BZR2 protein sequence resulted in 88% identity, (296/336) and 90% similarity (306/336). BZR2 (gi/8778414, gi/665069, and gi/15222005) is also the partial cDNA gi/13937167. Other homologs include gi/7485706, (the same as gi/15230298), gi/15234055, gi/15234528, and gi/15219156, gi/7485706, and gi/13937167.

Other computer program methods to determine identity and similarity between the two sequences include but are not limited to the GCG program package (Devereux, et al., *Nucl. Acids Res.* 12:387, 1984) and FASTA (Atschul, et al., *J Molec. Biol.* 215:403, 1990).

Antibodies

The invention provides antibodies immunoreactive with any BZR1 polypeptide, or antigenic fragments thereof One or more antibodies consisting essentially of pooled monoclonal antibodies with different epitopic specificities, as well as distinct monoclonal antibody preparations, are provided. Monoclonal antibodies are made from antigen containing fragments of the protein by methods well known to those skilled in the art (Kohler, et al., *Nature*, 256:495, 1975). Methods of making these fragments are known in the art. (See for example, Harlow and Lane, Antibodies: A Laboratory Manual, Cold Spring Harbor Laboratory, New York (1988), incorporated herein by reference).

The term "antibody" as used in this invention includes intact molecules as well as fragments thereof, such as Fab, F(ab')2, and Fv capable of binding to an epitopic determinant present in BZR1 polypeptide. Such antibody fragments retain some ability to selectively bind with its antigen or receptor.

As used in this invention, the term "epitope" refers to an antigenic determinant on an antigen to which the paratope of an antibody binds. Epitopic determinants often consist of chemically active surface groupings of molecules such as amino acids or sugar side chains and usually have specific three dimensional structural characteristics, as well as specific charge characteristics.

Antibodies which bind to the BZR1 polypeptide of the invention can be prepared using an intact polypeptide or fragments containing small peptides of interest as the immunizing antigen. For example, it may be desirable to produce antibodies that specifically bind to the N- or C-terminal domains of BZR1. The polypeptide or peptide used to immunize an animal may be derived from translated cDNA or may be chemically synthesized, and may further be conjugated to a carrier protein if desired. Commonly used carriers which are chemically coupled to an immunizing peptide include keyhole limpet hemocyanin (KLH), thyroglobulin, bovine serum albumin (BSA), and tetanus toxoid.

Polyclonal or monoclonal antibodies can be further purified, for example, by binding to and eluting from a matrix to which the polypeptide or a peptide to which the antibodies were raised is bound. Those of skill in the art are familiar with various techniques common in the immunology arts for purification and/or concentration of polyclonal antibodies, as well as monoclonal antibodies (See for example, Coligan, et al., Unit 9, Current Protocols in Immunology, Wiley Interscience, 1994, incorporated by reference).

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

A cDNA expression library such as lambda gt11, can be screened indirectly for BZR1 peptides using antibodies specific for BZR1 epitopes. Such antibodies may be polyclonally or monoclonally derived, and may be used to detect expression product indicative of the presence of BZR1 cDNA.

Screening for Molecules that Interact of Bind with Bzr1

In another series of embodiments, the present invention provides methods of screening or identifying proteins, small molecules or other compounds which are capable of inducing or inhibiting the expression of the BZR1 genes and proteins. The assays may be performed in vitro using transformed or non-transformed cells, immortalized cell lines, or in vivo using transformed plant models enabled herein. In particular, the assays may detect the presence of increased or decreased expression of BZR1 (from *Arabidopsis* or other plants) genes or proteins on the basis of increased or decreased mRNA expression, increased or decreased levels of BZR1 protein products, or increased or decreased levels of expression of a marker gene (e.g., beta-galactosidase, green fluorescent protein, alkaline phosphatase or luciferase) operably joined to a BZR1 5' regulatory region in a recombinant construct. Cells known to express a particular BZR1, or transformed to express a particular BZR1, are incubated and one or more test compounds are added to the medium. After allowing a sufficient period of time (anywhere from 0–72 hours or longer) for the compound to induce or inhibit the expression of BZR1, any change in levels of expression from an established baseline may be detected using any of the techniques described above.

In another series of embodiments, the present invention provides methods for identifying proteins and other compounds which bind to, or otherwise directly interact with, the BZR1 protein. The proteins and compounds will include endogenous cellular components which interact with BZR1 in vivo and which, therefore, provide new targets for agricultural products, as well as recombinant, synthetic and otherwise exogenous compounds which may have BZR1 binding capacity and, therefore, may be candidates for plant growth modulators. Thus, in one series of embodiments, high throughput screen (HTS) protein or DNA chips, cell lysates or tissue homogenates may be screened for proteins or other compounds which bind to one of the normal or mutant BZR1 genes. Alternatively, any of a variety of exogenous compounds, both naturally occurring and/or synthetic (e.g., libraries of small molecules or peptides), may be screened for BZR1 binding capacity.

In each of these embodiments, an assay is conducted to detect binding between BZR1 and some other moiety. The BZR1 in these assays may be any polypeptide comprising or derived from a normal or mutant BZR1 protein, including functional domains or antigenic determinants of the BZR1 fusion proteins. Binding may be detected by non-specific measures (e.g., transcription modulation, altered chromatin structure, peptide production or changes in the expression of other downstream genes which can be monitored by differential display, 2D gel electrophoresis, differential hybridization, or SAGE methods) or by direct measures such as immunoprecipitation, the Biomolecular Interaction Assay (BIAcore) or alteration of protein gel electrophoresis. The preferred methods involve variations on the following techniques: (1) direct extraction by affinity chromatography; (2) co-isolation of BZR1 components and bound proteins or other compounds by immunoprecipitation; (3) BIAcore analysis; and (4) the yeast two-hybrid systems.

In another series of embodiments, the present invention provides for methods of identifying proteins, small molecules and other compounds capable of modulating the activity of normal or mutant BZR1. Using normal cells or plants, the transformed cells and plant models of the present invention, or cells obtained from subjects bearing normal or mutant BZR1 genes, some embodiments of the present invention provide methods of identifying such compounds on the basis of their ability to affect the expression of BZR1, the activity of BZR1, the activity of other BZR1-regulated genes, the activity of proteins that interact with normal or mutant BZR1 proteins, the intracellular localization of the BZR1, changes in transcription activity, the presence or levels of BZR1, or other biochemical, histological, or physiological markers which distinguish cells bearing normal and modulated BZR1 activity in plants and in animals.

In accordance with another aspect of the invention, the proteins of the invention can be used as starting points for rational chemical design to provide ligands or other types of small chemical molecules. Alternatively, small molecules or other compounds identified by the above-described screening assays may serve as "lead compounds" in design of modulators brassinosteroid pathways in plants.

Bzr1 Polynucleotides

Specifically disclosed herein is a BZR1 genomic sequence (SEQ ID NO: 1). Embodiments of the invention also provide an isolated polynucleotide sequence encoding a polypeptide having the amino acid sequence of SEQ ID NO: 6. The term "isolated" as used herein includes polynucleotides substantially free of other nucleic acids, proteins, lipids, carbohydrates or other materials with which it is naturally associated. Polynucleotide sequences of the invention include DNA, cDNA and RNA sequences which encode BZR1. It is understood that polynucleotides encoding all or varying portions of BZR1 are included herein, as long as they encode a polypeptide with BZR1 activity. Such polynucleotides include naturally occurring, synthetic, and intentionally manipulated polynucleotides as well as splice variants. For example, portions of the mRNA sequence may be altered due to alternate RNA splicing patterns or the use of alternate promoters for RNA transcription. As used herein, the terms "polynucleotides" and "nucleic acid sequences" refer to DNA, RNA and cDNA sequences.

Specifically disclosed herein is a BZR1 cDNA sequence (SEQ ID NO 4). Embodiments of the invention include the coding regions of SEQ ID NOS: 4 and 5, which include nucleotides 233 to 1233 of SEQ ID NO: 4 and 233 to 1233 of SEQ ID NO: 5. The invention further includes the coding regions of SEQ ID NOS: 11 and 12, which include nucleotides 147–1154 of SEQ ID NO: 11 and nucleotides 147–1154 of SEQ ID NO: 12.

Included in embodiments of the invention are nucleotide sequences greater than 70% homologous to the sequence of SEQ ID NOs: 1, 2, 3, 4, 5, 9, 11, and 12 but still retain the ability to modulate plant growth. Other embodiments of the invention include nucleotide sequences that are greater than 75%, 80%, 85%, 90% or 95% homologous with the sequences of SEQ ID NOs: 1, 2, 3, 4, 5, 9, 11, and 12, but still retain the ability to modulate growth and development of plants.

In some embodiments, the BZR1 polynucleotides of the present invention include polynucleotides having alterations in the nucleic acid sequence, where such polynucleotides still encode a polypeptide having the ability to modulate responses to brassinosteroids. Alterations in BZR1 nucleic acid include but are not limited to intragenic mutations such as point mutations, nonsense (stop) mutations, antisense, splice site and frameshift mutations as well as heterozygous or homozygous deletions. Detection of such alterations can be done by standard methods known to those of skill in the art including sequence analysis, Southern blot analysis, PCR based analyses (e.g., multiplex PCR, sequence tagged sites (STSs)) and in situ hybridization. Embodiments of the invention also include anti-sense polynucleotide sequences, where an antisense sequence may be complementary to the entire sequence, or any fragment thereof.

The polynucleotides described herein include sequences that are degenerate as a result of the genetic code. There are 20 natural amino acids, most of which are specified by more than one codon. Therefore, all degenerate nucleotide sequences are included in the invention as long as the BZR1 polypeptide encoded by such nucleotide sequences retains BZR1 activity. A "functional polynucleotide" denotes a polynucleotide which encodes a functional polypeptide as described herein. Embodiments of the invention include polynucleotides encoding a polypeptide having the biological activity of the polypeptide having the amino acid sequence of SEQ ID NO: 6 and having at least one epitope for an antibody immunoreactive with BZR1 polypeptide.

The polynucleotide encoding BZR1 includes the nucleotide sequences in SEQ ID NOS: 1 and 4, as well as nucleic acid sequences complementary to that sequence. A complementary sequence may include an antisense nucleotide. When the sequence is RNA, the deoxyribonucleotides A, G, C, and T of SEQ ID NO: 1 are replaced by ribonucleotides A, G, C, and U, respectively. Also included in the invention are fragments ("probes") of the above-described nucleic acid sequences that are at least 15 bases in length, which is sufficient to permit the probe to selectively hybridize to DNA that encodes the protein of SEQ ID NO: 6.

DNA sequences of the invention can be obtained by several methods. For example, the DNA can be isolated using hybridization or computer-based techniques which are well known in the art. Such techniques include, but are not limited to: 1) hybridization of genomic or cDNA libraries with probes to detect homologous nucleotide sequences; 2) antibody screening of expression libraries to detect cloned DNA fragments with shared structural features; 3) polymerase chain reaction (PCR) on genomic DNA or cDNA using primers capable of annealing to the DNA sequence of interest; 4) computer searches of sequence databases for similar sequences; and 5) differential screening of a subtracted DNA library.

"Hybridization" refers to the process by which a nucleic acid strand joins with a complementary strand through base pairing. Hybridization reactions can be sensitive and selective so that a particular sequence of interest can be identified even in samples in which it is present at low concentrations. Suitably stringent conditions can be defined by, for example, the concentrations of salt or formamide in the prehybridization and hybridization solutions, or by the hybridization temperature, and are well known in the art. In particular, stringency can be increased by reducing the concentration of salt, increasing the concentration of formamide, or raising the hybridization temperature.

For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5×SSPE, 0.3% SDS, and 200 n/ml sheared and denatured salmon sperm DNA. Hybridization could occur under reduced stringency conditions as described above, but in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art.

"Selective hybridization" as used herein refers to hybridization under moderately stringent or highly stringent physiological conditions (See, for example, the techniques described in Maniatis et al., 1989 Molecular Cloning A Laboratory Manual, Cold Spring Harbor Laboratory, N.Y., incorporated herein by reference), which distinguishes related from unrelated BZR1 nucleotide sequences.

Screening procedures which rely on nucleic acid hybridization make it possible to isolate any gene sequence from any organism, provided the appropriate probe is available. Oligonucleotide probes corresponding to any part of a nucleotide sequence encoding a protein having BZR1 activity can be synthesized chemically. This requires that short, oligopeptide stretches of the amino acid sequence must be known. The DNA sequence encoding the protein can be deduced from the genetic code, and the degeneracy of the code must be taken into account. When the sequence is degenerate, it is possible to perform a mixed addition reaction, which includes a heterogeneous mixture of denatured double-stranded DNA. For screening procedures, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. By using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., Nucl. Acid Res., 9:879, 1981). Alternatively, a subtractive library, as illustrated herein is useful for elimination of non-specific cDNA clones.

Among the standard procedures for isolating cDNA sequences of interest is the formation of plasmid- or phage-carrying cDNA libraries which are derived from reverse transcription of mRNA from donor cells that have a high level of genetic expression. When used in combination with polymerase chain reaction technology, even low-abundance expression products can be cloned. In those cases where significant portions of the amino acid sequence of the polypeptide are known, the production of labeled single or double-stranded DNA or RNA probe sequences duplicating a sequence putatively present in the target cDNA may be employed in hybridization procedures carried out on copies of the cDNA which have been denatured to give single-stranded molecules (Jay, et al., Nucl. Acid Res., 11:2325, 1983).

Vectors

BZR1 polynucleotide sequences can be expressed in vitro by DNA transfer into a suitable host cell. "Host cells" are cells in which a vector can be propagated and its DNA expressed. The term also includes any progeny or graft material, for example, of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

The BZR1 polynucleotide sequences according to the present invention may be inserted into a recombinant expression vector. The terms "recombinant expression vector" or "expression vector" refer to a plasmid, virus or other vehicle known in the art that has been manipulated by insertion or incorporation of the BZR1 genetic sequence. Such expression vectors contain a promoter sequence which facilitates the efficient transcription of the inserted BZR1 sequence. The expression vector typically contains an origin of replication, a promoter, and one or more genes that allow phenotypic selection of the transformed cells.

Methods well-known to those skilled in the art can be used to construct expression vectors containing the BZR1 coding sequence and appropriate transcriptional/translational control signals. These methods include in vitro recombinant DNA techniques, synthetic techniques, and in vivo recombination/genetic techniques.

A variety of host-expression vector systems may be utilized to express the BZR1 coding sequence. These include, but are not limited to, microorganisms such as bacteria transformed with recombinant bacteriophage DNA, plasmid DNA or cosmid DNA expression vectors containing the BZR1 coding sequence; yeast transformed with recombinant yeast expression vectors containing the BZR1 coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the BZR1 coding sequence; insect cell systems infected with recombinant virus expression vectors (e.g., baculovirus) containing the BZR1 coding sequence; or animal cell systems infected with recombinant virus expression vectors (e.g., retroviruses, adenovirus, vaccinia virus) containing the BZR1 coding sequence, or transformed animal cell systems engineered for stable expression.

Depending on the host/vector system utilized, any of a number of suitable transcription and translation elements, including constitutive and inducible promoters, transcription enhancer elements, and/or transcription terminators, may be used in the expression vector (see e.g., Bitter, et al., Methods in Enzymology 153:516, 1987). For example, when cloning in bacterial systems, inducible promoters such as pL of bacteriophage γ, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the inserted BZR1 coding sequence.

Isolation and purification of recombinantly expressed polypeptide, or fragments thereof, provided by the invention, may be carried out by conventional means including chromatographic and immunological separations involving monoclonal or polyclonal antibodies.

Gene Transfer to Plants

In one embodiment of the present invention, one or more copies of the BZR1 or bzr1-D gene may be introduced into plants to create plants with high levels of BZR1 or bzr1-D polypeptide, using genetic modification techniques. One of skill in the art will recognize that the level of expression of BZR1 or bzr1-D may depend on many factors, including the number of copies of the inserted gene, the choice of promoter, and the location of gene insertion in the genome. Further, the cellular response to the inserted gene may depend on other cellular factors, such as the presence of suitable transcription factors, the presence or absence of interacting molecules, the choice of host plant, and the environmental conditions surrounding the plant. Examples of such environmental factors are light, temperature, nutrients, and water. One of skill in the art will appreciate the need to consider these factors when designing the genetic modification strategy.

The term "genetic modification" as used herein refers to the introduction of one or more heterologous nucleic acid sequences, e.g., a BZR1 encoding sequence, into one or more plant cells which can then be used to generate whole, sexually competent, viable plants. The term "genetically modified" as used herein refers to a plant which has been generated through the aforementioned process. Genetically modified plants of the invention are capable of self-pollinating or cross-pollinating with other plants of the same species so that the foreign gene, carried in the germ line, can be inserted into or bred into agriculturally useful plant varieties. The term "plant cell" as used herein refers to protoplasts, gamete-producing cells, and cells which regenerate into whole plants. Accordingly, a seed comprising multiple plant cells capable of regenerating into a whole plant, is included in the definition of "plant cell".

As used herein, the term "plant" refers to either a whole plant, a plant part, a plant cell, or a group of plant cells, such as plant tissue, for example. Plantlets are also included within the meaning of "plant". Plants included in the invention are any plants amenable to transformation techniques, including angiosperms, gymnosperms, monocotyledons and dicotyledons.

Examples of monocotyledonous plants include, but are not limited to, asparagus, field and sweet corn, barley, wheat, rice, sorghum, onion, pearl millet, rye and oats. Examples of dicotyledonous plants include, but are not limited to tomato, tobacco, cotton, rapeseed, field beans, soybeans, peppers, lettuce, peas, alfalfa, clover, cole crops or *Brassica oleracea* (e.g., cabbage, broccoli, cauliflower, brussel sprouts), radish, carrot, beets, eggplant, spinach, cucumber, squash, melons, cantaloupe, sunflowers and various ornamentals. Woody species include poplar, pine, sequoia, cedar, oak, fir, hemlock, ash, cherry, etc.

The term "heterologous nucleic acid sequence" as used herein refers to a nucleic acid foreign to the recipient plant host or, native to the host if the native nucleic acid is substantially modified from its original form. For example, the term includes a nucleic acid originating in the host species, where such sequence is operably linked to a promoter that differs from the natural or wild-type promoter. In the broad method of the invention, at least one nucleic acid sequence encoding BZR1 is operably linked with a promoter. It may be desirable to introduce more than one copy of BZR1 polynucleotide into a plant for enhanced BZR1 expression. For example, multiple copies of the gene would have the effect of increasing production of BZR1 in the plant.

It may also be desirable to decrease levels of BZR1 in plant. For example, dwarf plants or plants with specifically dwarfed organs may result from down-regulating BZR1 gene expression. Any method to downregulate BZR1 gene expression may be used, but typical examples include antisense technology, cosuppression, RNA inhibition (RNAi), and ribozyme inhibition.

Antisense-based reduction of gene expression can be achieved by integration of heterologous DNA under the transcriptional control of a promoter which is functional in the host, and in which the transcribed strand of heterologous DNA is complementary to the strand of DNA that is transcribed from the endogenous gene to be regulated. The introduced DNA, referred to as antisense DNA, provides an RNA sequence which is complementary to naturally produced (endogenous) mRNAs and which inhibits expression of the endogenous mRNA. The antisense product may be complementary to coding or non-coding (or both) portions of naturally occurring target RNA. It is most preferred that the antisense sequence utilized be complementary to the endogenous sequence, however, minor variations in the exogenous and endogenous sequences may be tolerated. An antisense polynucleotide can be introduced to a cell by introducing an expressible construct containing a nucleic acid segment that codes for the polynucleotide.

Antisense molecules introduced into cells that contain BZR1, for example, may function by decreasing the amount of BZR1 expression in a cell, or may function by a different mechanism. Antisense BZR1 polynucleotides useful for the present invention are complementary to specific regions of the corresponding endogenous target BZR1 mRNA. Antisense polynucleotides in context of the present invention may include short sequences of nucleic acid known as oligonucleotides, usually 10–50 bases in length, as well as longer sequences of nucleic acid that may exceed the length of the BZR1 gene sequence itself.

Genetically modified plants are produced by contacting a plant cell with a vector including at least one nucleic acid sequence encoding BZR1. To be effective once introduced into plant cells, the BZR1 nucleic acid sequence must be operably associated with a promoter which is effective in the plant cells to cause transcription of BZR1. Additionally, a polyadenylation sequence or transcription control sequence recognized in plant cells may be employed. It is preferred that the vector harboring the nucleic acid sequence to be inserted also contain one or more selectable marker genes so that the transformed cells can be selected from non-transformed cells in culture, as described herein.

The term "operably associated" refers to functional linkage between a promoter sequence and the BZR1 nucleic acid sequence regulated by the promoter. The operably linked promoter controls the expression of the BZR1 nucleic acid sequence.

The expression of structural genes employed in the present invention may be driven by a number of promoters. The endogenous, or native promoter of a structural gene of interest may be utilized for transcriptional regulation of the gene, or the promoter may be a foreign regulatory sequence. For plant expression vectors, suitable viral promoters include the 35S RNA and 19S RNA promoters of CaMV (Brisson, et al., Nature, 310:511, 1984; Odell, et al., Nature, 313:810, 1985); the full-length transcript promoter from Figwort Mosaic Virus (FMV) (Gowda, et al., J. Cell Biochem., 13D: 301, 1989) and the coat protein promoter to TMV (Takamatsu, et al., EMBO J. 6:307, 1987). Alternatively, plant promoters such as the light-inducible promoter from the small subunit of ribulose bis-phosphate carboxylase (ssRUBISCO) (Coruzzi, et al., EMBO J., 3:1671, 1984; Broglie, et al., Science, 224:838, 1984); mannopine synthase promoter (Velten, et al., EMBO J., 3:2723, 1984) nopaline synthase (NOS) and octopine synthase (OCS) promoters (carried on tumor-inducing plasmids of Agrobacterium tumefaciens) or heat shock promoters, e.g., soybean hsp17.5-E or hsp17.3-B (Gurley, et al., Mol. Cell. Biol., 6:559, 1986; Severin, et al., Plant Mol. Biol., 15:827, 1990) may be used.

Promoters useful in the invention include both natural constitutive and inducible promoters as well as engineered promoters. In general, a constitutive promoter results in continuous transcription of the gene. The CaMV promoters are examples of constitutive promoters. Inducible promoters, in contrast, are generally not active unless they are induced by chemical or environmental means. To be most useful, an inducible promoter should 1) provide low expression in the absence of the inducer; 2) provide high expression in the presence of the inducer; 3) use an induction scheme that does not interfere with the normal physiology of the plant; and 4) have no effect on the expression of other genes. Examples of inducible promoters useful in plants include those induced by chemical means, such as the yeast metallothionein promoter which is activated by copper ions (Mett, et al., Proc. Natl. Acad. Sci., U.S.A., 90:4567, 1993); In2-1 and In2-2 regulator sequences which are activated by substituted benzenesulfonamides, e.g., herbicide safeners (Hershey, et al., Plant Mol. Biol., 17:679, 1991); and the GRE regulatory sequences which are induced by glucocorticoids (Schena, et al., Proc. Natl. Acad. Sci., U.S.A., 88:10421, 1991). Other promoters, both constitutive and inducible will be known to those of skill in the art.

The particular promoter selected should be capable of causing sufficient expression to result in the production of an effective amount of structural gene product, e.g., BZR1, to cause increased plant size and/or cell size. The promoters used in the vector constructs may be modified, if desired, to affect their control characteristics.

Tissue specific promoters may also be utilized in the present invention. An example of a tissue specific promoter is the promoter active in shoot meristems (Atanassova, et al., Plant J., 2:291, 1992). Other tissue specific promoters useful in transgenic plants, including the cdc2a promoter and cyc07 promoter, will be known to those of skill in the art. (See for example, Ito, et al., Plant Mol. Biol., 24:863, 1994; Martinez, et al., Proc. Natl. Acad. Sci. USA, 89:7360, 1992; Medford, et al., Plant Cell, 3:359, 1991; Terada, et al., Plant Journal., 3:241, 1993; Wissenbach, et al., Plant Journal, 4:411, 1993).

The upstream regions that control expression of the BZR1 gene may contain more than one promoter, and may additionally contain one or more enhancer elements. Such regions may be present, for example, in activation-tagging vectors (Weigel, et al., Plant Physiol. 122:1003, 2000), which contain multimerized transcriptional enhancers from the cauliflower mosaic virus (CaMV) 35S gene.

Optionally, a selectable marker may be associated with the nucleic acid sequence to be inserted. As used herein, the term "marker" refers to a gene encoding a trait or a phenotype which permits the selection of, or the screening for, a plant or plant cell containing the marker. The marker gene may be an antibiotic resistance gene whereby the appropriate antibiotic can be used to select for transformed cells from among cells that are not transformed. Examples of suitable selectable markers include adenosine deaminase, dihydrofolate reductase, hygromycin-B-phospho-transferase, thymidine kinase, xanthine-guanine phospho-ribosyltransferase and amino-glycoside 3'-O-phospho-transferase II (kanamycin, neomycin and G418 resistance). Other suitable markers will be known to those of skill in the art.

Vector(s) employed in the present invention for transformation of a plant cell include a nucleic acid sequence encoding BZR1, operably associated with a promoter. To commence a transformation process in accordance with the present invention, it is first necessary to construct a suitable vector and properly introduce it into the plant cell. Details of the construction of vectors utilized herein are known to those skilled in the art of plant genetic engineering.

BZR1 nucleic acid sequences utilized in the present invention can be introduced into plant cells using Ti plasmids of *Agrobacterium tumefaciens*, root-inducing (Ri) plasmids, and plant virus vectors. (For reviews of such techniques see, for example, Weissbach & Weissbach, 1988, Methods for Plant Molecular Biology, Academic Press, NY, Section VIII, pp. 421–463; and Grierson & Corey, 1988, Plant Molecular Biology, 2d Ed., Blackie, London, Ch. 7–9, and Horsch, et al., *Science*, 227:1229, 1985, both incorporated herein by reference). In addition to plant transformation vectors derived from the Ti or root-inducing (Ri) plasmids of *Agrobacterium*, alternative methods may involve, for example, the use of liposomes, electroporation, chemicals that increase free DNA uptake, transformation using viruses or pollen and the use of microprojection.

One of skill in the art will be able to select an appropriate vector for introducing the BZR1-encoding nucleic acid sequence in a relatively intact state. Thus, any vector which will produce a plant carrying the introduced DNA sequence should be sufficient. Even use of a naked piece of DNA would be expected to confer the properties of this invention, though at low efficiency. The selection of the vector, or whether to use a vector, is typically guided by the method of transformation selected.

The transformation of plants in accordance with the invention may be carried out in essentially any of the various ways known to those skilled in the art of plant molecular biology. (See, for example, Methods of Enzymology, Vol. 153, 1987, Wu and Grossman, Eds., Academic Press, incorporated herein by reference). As used herein, the term "transformation" means alteration of the genotype of a host plant by the introduction of BZR1 nucleic acid sequence.

For example, a BZR1 nucleic acid sequence can be introduced into a plant cell utilizing *Agrobacterium tumefaciens* containing the Ti plasmid, as mentioned briefly above. In using an *A. tumefaciens* culture as a transformation vehicle, it is most advantageous to use a non-oncogenic strain of *Agrobacterium* as the vector carrier so that normal non-oncogenic differentiation of the transformed tissues is possible. It is also preferred that the Agrobacterium harbor a binary Ti plasmid system. Such a binary system comprises 1) a first Ti plasmid having a virulence region essential for the introduction of transfer DNA (T-DNA) into plants, and 2) a chimeric plasmid. The latter contains at least one border region of the T-DNA region of a wild-type Ti plasmid flanking the nucleic acid to be transferred. Binary Ti plasmid systems have been shown effective to transform plant cells (De Framond, *Biotechnology*, 1: 262, 1983; Hoekema, et al., *Nature*, 303:179, 1983). Such a binary system is preferred because it does not require integration into the Ti plasmid of *Agrobacterium*, which is an older methodology.

Methods involving the use of *Agrobacterium* in transformation according to the present invention include, but are not limited to: 1) co-cultivation of *Agrobacterium* with cultured isolated protoplasts; 2) transformation of plant cells or tissues with *Agrobacterium*; or 3) transformation of seeds, apices or meristems with *Agrobacterium*.

In addition, gene transfer can be accomplished by in planta transformation by *Agrobacterium*, as described by Bechtold, et al., (*C. R. Acad. Sci.* Paris, 316:1194, 1993) and exemplified in the Examples herein. This approach is based on the vacuum infiltration of a suspension of *Agrobacterium* cells.

The preferred method of introducing BZR1-encoding nucleic acid into plant cells is to infect such plant cells, an explant, a meristem or a seed, with transformed *Agrobacterium tumefaciens* as described above. Under appropriate conditions known in the art, the transformed plant cells are grown to form shoots, roots, and develop further into plants.

Alternatively, BZR1 encoding nucleic acid sequences according to the present invention can be introduced into a plant cell using mechanical or chemical means. For example, the nucleic acid can be mechanically transferred into the plant cell by microinjection using a micropipette. Alternatively, the nucleic acid may be transferred into the plant cell by using polyethylene glycol which forms a precipitation complex with genetic material that is taken up by the cell.

BZR1 nucleic acid sequences according to the present invention can also be introduced into plant cells by electroporation (Fromm, et al., *Proc. Natl. Acad. Sci., U.S.A.*, 82:5824, 1985, which is incorporated herein by reference). In this technique, plant protoplasts are electroporated in the presence of vectors or nucleic acids containing the relevant nucleic acid sequences. Electrical impulses of high field strength reversibly permeabilize membranes allowing the introduction of nucleic acids. Electroporated plant protoplasts reform the cell wall, divide and form a plant callus. Selection of the transformed plant cells with the transformed gene can be accomplished using phenotypic markers as described herein.

Another method for introducing BZR1 nucleic acid into a plant cell is by means of high velocity ballistic penetration by small particles with the nucleic acid to be introduced contained either within the matrix of such particles, or on the surface thereof (Klein, et al., *Nature* 327:70, 1987). Bombardment transformation methods are also described in Sanford, et al. (*Techniques* 3:3, 1991) and Klein, et al. (*Bio/Techniques* 10:286, 1992). Although typically, only a single introduction of a new nucleic acid sequence is required, this method particularly provides for multiple introductions.

Cauliflower mosaic virus (CaMV) may also be used as a vector for introducing nucleic acid into plant cells (U.S. Pat. No. 4,407,956). CaMV viral DNA genome is inserted into a parent bacterial plasmid creating a recombinant DNA molecule which can be propagated in bacteria. After cloning, the recombinant plasmid again may be cloned and further modified by introduction of the desired nucleic acid sequence. The modified viral portion of the recombinant plasmid is then excised from the parent bacterial plasmid, and used to inoculate the plant cells or plants.

As used herein, the term "contacting" refers to any means of introducing BZR1 into the plant cell, including chemical and physical means as described above. Preferably, contacting refers to introducing the nucleic acid or vector into plant cells (including an explant, a meristem or a seed), via *Agrobacterium tumefaciens* transformed with the BZR1 encoding nucleic acid as described above.

Plant Regeneration

Normally, a plant cell is regenerated to obtain a whole plant from the transformation process. The immediate product of the transformation is referred to as a "transgenote". The term "growing" or "regeneration" as used herein means growing a whole plant from a plant cell, a group of plant cells, a plant part (including seeds), or a plant piece (e.g., from a protoplast, callus, or tissue part).

Regeneration from protoplasts varies from species to species of plants, but generally a suspension of protoplasts is first made. In certain species, embryo formation can then be induced from the protoplast suspension, to the stage of ripening and germination as natural embryos. The culture media will generally contain various amino acids and hormones, necessary for growth and regeneration. Examples of hormones utilized include auxins and cytokinins. It is sometimes advantageous to add glutamic acid and proline to the medium, especially for plant species such as corn and alfalfa. Efficient regeneration will depend on the medium, on the genotype, and on the history of the culture. If these variables are controlled, regeneration is reproducible.

Regeneration also occurs from plant callus, explants, organs or parts. Transformation can be performed in the context of organ or plant part regeneration (see Methods in Enzymology, Vol. 118 and Klee, et al., Annu. Rev. Plant Physiol., 38:467, 1987). Utilizing the leaf disk-transformation-regeneration method of Horsch, et al., Science, 227:1229, 1985, disks are cultured on selective media, followed by shoot formation in about 2–4 weeks. Shoots that develop are excised from calli and transplanted to appropriate root-inducing selective medium. Rooted plantlets are transplanted to soil as soon as possible after roots appear. The plantlets can be repotted as required, until reaching maturity.

In vegetatively propagated crops, the mature transgenic plants are propagated by utilizing cuttings or tissue culture techniques to produce multiple identical plants. Selection of desirable transgenotes is made and new varieties are obtained and propagated vegetatively for commercial use.

In seed propagated crops, the mature transgenic plants can be self crossed to produce a homozygous inbred plant. The resulting inbred plant produces seed containing the newly introduced foreign gene(s). These seeds can be grown to produce plants that would produce the selected phenotype, e.g. increased plant size.

Parts obtained from regenerated plant, such as flowers, seeds, leaves, branches, roots, fruit, and the like are included in the invention, provided that these parts comprise cells that have been transformed as described. Progeny and variants, and mutants of the regenerated plants are also included within the scope of the invention, provided that these parts comprise the introduced nucleic acid sequences. Plants exhibiting increased size as compared with wild-type plants can be selected by visual observation. The invention includes plants produced by the method of the invention, as well as plant tissue and seeds.

Agronomic Utility

Agronomic Utility of Plants with Altered Levels of BZR1 or bzr1-D Polypeptide

Overexpression of the mutant bzr1-D produced cells which are larger than control cells, a phenotype which may be particularly useful for agronomic purposes. Accordingly, one embodiment of the present invention provides a method for producing a genetically modified plant cell such that a plant produced from said cell produces plants that are larger in size as compared with wild-type plants. The method includes contacting the plant cell with a BZR1 nucleic acid sequence to obtain a transformed plant cell; growing the transformed plant cell under plant forming conditions to obtain a plant having increased size.

In yet another embodiment, the invention provides a method for producing a genetically modified plant characterized as having increased yield as compared to a plant which has not been genetically modified (e.g., a wild-type plant). The term "yield" has been previously defined herein. The method includes the steps of contacting a plant cell with at least one vector containing at least one nucleic acid sequence encoding a BZR1 polypeptide according to the present invention, wherein the nucleic acid sequence is operably associated with a promoter, to obtain a transformed plant cell; producing a plant from the transformed plant cell; and thereafter selecting a plant exhibiting increased yield.

In yet another embodiment, the invention provides for genetic modifications to result in plants with reduced levels of BZR1 or BZR2 polypeptides. The reduction in BZR1 or BZR2 levels could be achieved, for example, using antisense technology. Resulting plants would be expected to be smaller in overall size, with lower biomass yield and decreased sizes of individual cells or tissues. Smaller plants may be useful, for example, in situations where limited growing space is available.

Agronomic Utility of BZR1 Conditional Expression

Conditional expression, such as inducible expression or tissue-specific expression of this gene may also be of agronomic use. Therefore, in another embodiment, the invention provides a method of producing a plant characterized as having increased size by contacting a susceptible plant with a BZR1 promoter-inducing amount of an agent which induces BZR1 gene expression, wherein induction of BZR1 gene expression results in production of a plant having increased size as compared to a plant not contacted with the agent. A "susceptible plant" refers to a plant that can be induced to utilize its endogenous BZR1 gene to achieve increased size. The term "promoter inducing amount" refers to that amount of an agent necessary to elevate BZR1 gene expression above the level of BZR1 expression in a plant cell not contacted with the agent. For example, a transcription factor or a chemical agent may be used to elevate gene expression driven by a BZR1 native promoter, thereby inducing promoter activity and BZR1 gene expression.

The bzr1-D gene may be operably linked to an inducible promoter. Many types of inducible promoters are known, including those that are induced by environmental conditions such as drought, cold, salt stress, heat, or nutrient stress. Promoters which are induced by exogenous applications of a compound may also be operably linked to the bzr1-D gene. Other modifications could be made to comply with specific environmental or developmental needs of the crop to be modified.

The BZR1 gene may also be operably linked to environmentally inducible promoters to produce crops with agricultural characteristics that are regulated by environmental conditions. For example, the BZR1 gene could be linked to both cold-specific promoters and seed specific promoters so that when cold weather begins, BZR1 is highly expressed in the seed, signaling more of the crop's biomass to accumulate in the seed rather than in unusable leaf material which will die when colder weather arrives. In contrast, the BZR1 gene could be linked to root-specific promoters and drought-specific promoters such that, upon water stress, growth is focused toward more root growth to increase water uptake. This may result in increased survival under poor environmental conditions.

Crops containing a high level of the BZR1 protein may also require larger nutrient inputs or increased water. Therefore, in some cases it may be useful to link the BZR1 gene to heterologous promoters such that the BZR1 protein is highly expressed when abundant water and nutrients are available, but is downregulated under water or nutrient stress. This would potentially increase the plasticity of the system by making plants more resistant to natural changes in weather cycles or to changes in fertilizer application strategies.

As an example of the usefulness of tissue-specific expression of the bzr1-D gene, it may be useful to combine the mutant bzr1-D gene with tissue-specific promoters to target specific plant tissues in which larger cells would be advantageous. The combination of the bzr1-D gene with a fruit-specific promoter could be used to create larger fruit. Similarly, operably linking an influorescence-specific promoter to the bzr1-D gene may result in plants with larger flowers. In another example, combining the bzr1-D gene with root-specific promoters could result in larger roots.

Phenotypic Analysis

The phenotypic observation of plants transformed with BZR1, bzr1-D, BZR2, and bzr2-D genes further clarifies the effects of these genes on brassinosteroid pathways and plant growth. Arabidopsis plants overexpressing these genes may be measured to quantify phenotypic alterations such as leaf size, leaf width, plant height, and the size of individual cells in comparison with that of non-transformed control plants (Table 2, Example 8).

For example, overexpression of the BZR1 gene causes a slight increase in hypocotyl and petiole elongation. On a whole plant scale, overexpression of the BZR1 gene results in plants with a larger overall size. Interestingly, overexpression of the bzr1-D or bzr2-D mutant genes results in an even more dramatic increase in overall plant growth as well as increased growth and elongation of individual cells and plant tissues (see Table 2).

Analysis of phenotypes of double mutants may also be useful to elucidate brassinosteroid pathway interactions. For example, the expression of the bzr1-D mutant in other mutant backgrounds is useful for determining the placement of this gene in the brassinosteroid pathway. When the bzr1-D mutant gene is expressed in a det2 mutant background or a bri1 mutant background, the de-etiolation phenotypes of det2 and bri1 are suppressed (Table 3), suggesting that it acts downstream of the brassinosteroid receptor. The bzr1-D mutant, in fact, appears to replace receptor function. Furthermore, in an embodiment of the invention, the bzr1-D mutant can be used as a probe to find other genes and proteins involved in the brassinosteroid pathway.

The above disclosure generally describes the present invention. A more complete understanding can be obtained by reference to the following specific examples which are provided herein for purposes of illustration only and are not intended to limit the scope of the invention.

EXAMPLE 1

Plant Material and Growth Conditions

Arabidopsis seeds (Columbia ecotype) were surface sterilized by washing for 20 min in 70% (v/v) ethanol containing 0.05% (v/v) Triton X-100, followed by a wash with 95% (v/v) ethanol. Seeds were dried on filter paper and sown on 0.5× Murashige-Skoog medium (Gibco-BRL, Cleveland) supplemented with 1% (v/v) Sucrose and 0.8% (v/v) phytoagar. The plates were wrapped in aluminum foil and left at 4° C. overnight to induce germination. Seedlings were grown in growth chambers at 21° C. under long-day conditions (16 h of light/8 hours of dark).

EXAMPLE 2

Generation of Arabidopsis Mutations using an EMS Mutagenesis Approach

The bzr1-D mutation was isolated from a set of several thousand Arabidopsis seeds mutagenized by ethane methyl sulphonate using the following procedure. 0.2 gram of Arabidopsis seed (10,000 seeds total) was washed in 0.1% Tween for 15 minutes, followed by a 15 minute wash in ddH$_2$O. Seeds were than placed in 15 ml ddH$_2$O containing 15–45 μl ethane methyl sulphonate (EMS) (0.1% to 0.3%), and incubated at 23° C. for 10 hours with constant rotation in a fume hood. Seeds were then rinsed in ddH$_2$O for 4 hours with several changes of H$_2$O to completely remove EMS. Seeds were then sown on 0.1% Agar.

EXAMPLE 3

Screening of Mutants using a Brassinosteroid Inhibitor

The mutagenized plants were put through a screening procedure based on the use of brassinazole, a triazole-type brassinosteroid biosynthesis inhibitor (Asami, et al., *Plant Physiol.* 123: 93, 2000). Brassinazole application to normal Arabidopsis plants usually results in dwarfism, altered leaf morphology, darker greening of leaves, and decreased hypocotyl length. Mutagenized Arabidopsis plants that did not exhibit these characteristics when brassinazole was applied were examined further. One of these brassinazole-insensitive mutants was found to contain the bzr1-D mutation (SEQ ID NO 2).

EXAMPLE 4

Phenotype of the bzr1-D Mutant

The dark-grown bzr1-D mutant is insensitive to brassinazole inhibition of hypocotyl elongation. The bzr1-D mutant has a curly hypocotyl similar to that of a seedling grown on medium containing brassinosteroids. These characteristics are listed in Table 1, below.

TABLE 1

Phenotype of bzr1-D mutant

| Phenotype | Light-grown | Dark-grown |
|---|---|---|
| Bassinazole sensitivity | partially sensitive | insensitive |
| Hypocotyl morphology | no effect | curly |
| Leaf size (compared to WT) | larger | N/A |
| Flowering time | delayed | N/A |

EXAMPLE 5

Identification of the BZR1 Gene and the bzr1-D Mutation

The BZR1 gene was identified by map-based cloning (Li and Chory, Cell 90, 929-938, 1997; Lukowitz et al., Plant Physiol. 123, 795–805, 2000). The bzr1-D mutant, which is in Columbia ecotype, was crossed with Arabidopsis thaliana Landsberg ecotype, and the F1 plants were self-pollinated to generate F2 plants segregating the bzr1-D and wild type plants. The F2 plants were grown on brassinazole medium, and seedlings with wild type phenotype (short hypocotyls and open cotyledons, BZR1/BZR1 genotype) were selected for analysis of SSLP and CAPS markers. Analysis of DNAs from 50 F2 plants identified the nga111 marker on the chromosome I to be linked to the bzr1 locus. DNAs were then isolated from a total of 2200 individual F2 plants and analyzed for SSLP and CAPS markers around the nga111 marker. After scoring 4016 chromosomes, the bzr1 mutation was mapped to a 14.5 kilobase region on the sequenced BAC clone F9E10 (AC013258). The annotated open reading frame sequences within this region were amplified by polymerase chain reaction (PCR) from the bzr1-D genomic DNA, the PCR products were sequenced at the DNA sequencing facility at the Salk Institute, and the sequences were compared with the sequence of BAC clone F9E10 (AC013258).

We found a single base change of G to A in the DNA of bzr1-D at a position corresponding to nucleotide 16614 of BAC clone F9E10 (AC013258). This sequence change is within an open-reading-frame (AC013258_7) and is predicted to change the codon for amino acid proline to a codon for amino acid leucine, at position 231 of the predicted amino acid sequence encoded by this gene (AC013258_7). When we did a BLAST search of the EST database and compared the sequences of the EST clones (AV551486, AV442375) and the annotated BAC sequence, we found an error in the annotation of this gene. Based on the EST sequence, the intro-exon junction should be between nucleotides 17046 and 17047, rather than 17037 and 17038 of F9E10. The annotation of the BAC sequence caused a deletion of 9 bp coding sequence (3 amino acids in predicted protein sequence). Thus the proline amino acid affected in the bzr1-D mutant should be at amino acid position 234, rather than 231.

EXAMPLE 6

Sequence Comparison of BZR1 with Other Known Proteins

BLAST (Basic Local Alignment Search Tool) is a computer-automated amino acid sequence and nucleic acid sequence comparison and identification tool. The heuristic search algorithm BLAST 2.2.1 (Altschul. et al., Nucleic Acids Res. 25:3389, 1997; Altschul, et al., J. Mol. Biol 215:403, 1990; and Madden, et ml. Meth. Enzymol. 266:131, 1996, incorporated herein by reference) was used to search for proteins sintilar to the BZR1 protein sequence. The BLASTP tool (available on the world wide web at ncbi.nih.gov/BLAST) takes protein sequences in FASTA format, GenBank Accession numbers or GI numbers and compares them against the NCBI protein databases.) The BZR1 sequence was quoricd against the non-redundant database using the standard protein-protein BLASTP version 2.2.1 (Apr. 13, 2001) with the following settings: matrix=BLOSUM62, gap costs: Existence; 11, Extension: 1. The % identity and % similarity (positives) measurements were determined by a pairwise blast search "BLAST 2 sequences" results version BLAST))"(Tatusova, et al., FEMS Microbiol Lett. 174:247, 1999, incorporated herein by reference).

EXAMPLE 7

Production of Transgenic Arabidopsis Plants Containing the BZR1 Sequence

To confirm that the single base pair mutation in the BZR1 gene is responsible for the bzr1-D phenotype, the BZR1 gene carrying the mutation was transformed into wild type Arabidopsis plants. The bzr1-D mutant is dominant, so the mutant gene was expected to cause the bzr1-D phenotype when introduced into wild type plants. The coding sequence of the wild type (BZR1) or the mutant version of the BZR1 gene (bzr1-D) was amplified from DNA extracted from either wild type or the bzr1-D mutant plants, respectively, using primers BZ5K (tctggtacccacctattcaaagc) (SEQ ID NO: 13) and BZ3B (tgaggatccactctaacactcccaatg) (SEQ ID NO: 14). The PCR products were digested with restriction enzymes KpnI and BamHI, and ligated into the binary vector pCHF3 at corresponding sites downstream of the 35S promoter.

The constructs were transformed into Arabidopsis using Agrobacterium-mediated transformation. Arabidopsis thaliana (Columbia wild-type strain Col-7) plants were grown at 23° C. in long-day conditions (16 h of light and 8 h of dark) under a mixture of 3:1 cool-white:Gro-Lux fluorescent lights (Osram Sylvania, Danvers, Mass.). The BZR1 gene construct was then transformed to Arabidopsis using Agrobacterium-mediated transformation. Seeds from the Agrobacterium-treated plants were mixed with 0.1% (w/v) Phytagar(Gibco, Rockville, Md.), incubated at 4° C. for 2 d for stratification, and sown directly on soil. The wild type plants transformed with the mutant BZR1 gene caused brassinazole insensitive phenotype similar to the bzr1-D mutant, demonstrating that this gene is the BZR1 gene and the proline 234 to leucine mutation of BZR1 is responsible for the bzr1-D mutant phenotypes.

EXAMPLE 8

Observation of Plants Transformed with BZR1, bzr1-D, BZR2, and bzr2-D Genes

We have generated homozygous transgenic Arabidopsis plants that express BZR1, BZR2, bzr1-D and bzr2-D genes from their corresponding promoters or the constitutive 35S promoter. The results are summarized in Table 2. Expression of wild type BZR1 and BZR2 genes from their own promoters did not cause obvious phenotypes. Overexpression of the BZR1 gene slightly increased hypocotyl and petiole elongation. Expression of the mutant bzr1-D and bzr2-D genes increased cell elongation causing phenotypes of long hypocotyls, long petioles, long stems, bigger siliques, and larger leaves. Overexpression of the mutant form of bzr1-D or bzr2-D proteins causes dramatic phenotypes of increased growth and cell elongation in various organs and tissues, including hypocotyls, petioles, leaf blades, stems, pedicels, and siliques.

TABLE 2

Phenotypes of plants transformed with BZR1, bzr1-D, BZR2, and bzr2-D genes

| Transgene | Light-grown | Dark-grown |
| --- | --- | --- |
| 35S:BZR1 or 35S:BZR2 | No effect | On brassinazole, longer hypocotyls than wild type |
| 35S:bzr1-D or 35S:bzr2-D | Leaf epinasty, longer hypocotyls; elongated stem, pedicels, and siliques. Delayed flowering | Same as bzr1-D mutant. Insensitive to brassinazole |

EXAMPLE 9

Use of Double Mutants to Elucidate Brassinosteroid Pathway Interactions

Expression of the brz1-D mutant in other mutant backgrounds is useful for determining the placement of this gene in the brassinosteroid pathway. Expression of brz1-D mutant suppresses the phenotypes of det2 and bri1 mutants (Table 3). Therefore, it is thought to act downstream of the brassinosteroid receptor. The bzr1-D mutant, in fact, appears to replace receptor function. In an embodiment of the invention, the bzr1-D mutant can be used as a probe to find other genes and proteins involved in the brassinosteroid pathway.

TABLE 3

Phenotypes of constitutively overexpressed 35S:bzr1-D in other brassinosteroid mutant backgrounds

| Transgene | Light-grown | Dark-grown |
|---|---|---|
| 35S:bzr1-D in det2 mutant | Suppresses the det2 phenotype | bzr1-D phenotype. Suppresses det2 mutant phenotype |
| 35S:bzr1-D in bri1 mutant | Suppresses the bri1 phenotype | bzr1-D phenotype. Suppresses bri1 mutant phenotype. |

EXAMPLE 10

Construction of BZR1::CFP and bzr1-D::CFP and Subcellular Localization

The BZR1 protein sequence was found to contain a putative nuclear localization signal sequence. To test whether native BZR1 is involved in nuclear activities, transgenic plants carrying translational fusions of BZR1 or bzr1-D to the fluorescent protein CFP were examined for alterations in subcellular localization.

The entire BZR1 (or bzr1-D) coding region was fused to CFP following general molecular biology methods. The construct was transferred to *Agrobacterium tumefaciens* and transformed to wild-type *Arabidopsis* plants by vacuum infiltration. Transformed seedlings were selected on 0.5× Murashige-Skoog medium, 1% (w/v) sucrose, 0.8% (w/v) phytagar, and 50 μg/mL kanamycin. Plants were then propagated on soil. Confocal and conventional fluorescence microscopy were performed on an IX70 inverted microscope (Olympus, Tokyo) using a fluorescein isothiocyanate filter set (Olympus).

Both wild type BZR1-CFP and the mutant bzr1-D::CFP fusion proteins are localized in the nucleus in both light-grown and dark-grown tissues (Table 4). Overall, the mutant bzr1-D::CFP transgenic lines showed higher CFP signals than the wild type BZR1-CFP lines, suggesting that bzr1-D mutation may increase the stability as well as the activity of the protein.

TABLE 4

Phenotypes of BZR1::CFP and bzr1-D::CFP transgenic plants.

| Transgene | BZR1-CFP | bzr1-D::CFP |
|---|---|---|
| In wild type background | No phenotype | 1. bzr1-D phenotype, 2. Increased size of leaves, petioles, stem, and siliques. 3. Changes in greening. 4. Delayed flowering |
| In bri1 mutant background | No change of phenotype from bri1. | Suppresses bri1 phenotypes. |

EXAMPLE 11

Morphometric Analysis of Transgenic *Arabidopsis* Expressing BZR1 or bzr1-D is Expected to Result in Larger Plants and Larger Plant Organs

*Arabidopsis* plants overexpressing the BZR1 gene are expected to have a larger overall plant size. To determine whole plant and individual cell size changes, *Arabidopsis* plants overexpressing the BZR1 gene and *Arabidopsis* control plants are grown by the following method. Approximately 20 seeds were planted in 10 cm pots with soil presoaked in water. Plants are grown under a 16 hour light/9 hour dark cycle, irrigating with water or Hoagland's nutrient solution as necessary. Seedlings are thinned to four or five well-spaced seedlings per pot. After 5 weeks, plants are harvested and hypocotyl length, leaf blade length, leaf width, petiole length, and plant height are measured to the nearest millimeter using a ruler. An estimate of cellular size changes of individual cells may be measured by digital imaging of tissue slices or epidermal cells, followed by calculating cellular area using image processing programs such as Image-Pro. Typical results expected are listed in Table 5, below. Measurements are calculated as a percentage of the control plant.

TABLE 5

Morphometric analysis of altered BZR1 gene expression

| Transformed gene | Hypocotyl Length | Leaf Blade length | Leaf Width | Petiole Length | Plant Height |
|---|---|---|---|---|---|
| BZR1 | 115% | 115% | 115% | 115% | 115% |
| brz1-D | 135% | 135% | 135% | 135% | 135% |
| control | 100% | 100% | 100% | 100% | 100% |

What is claimed is:

1. An isolated nucleic acid molecule encoding the bzr1-D polypeptide having the amino acid sequence of SEQ ID NO:7.

2. The nucleic acid of claim 1, wherein said nucleic acid molecule comprise the nucleotide sequence of SEQ ID NO: 2.

3. A vector comprising the nucleic acid molecule of claim 1.

4. A vector comprising the nucleic acid molecule of claim 2.

5. A host cell comprising the vector of claim 3.

6. A host cell comprising the vector of claim 4.

7. A transgenic plant transformed with the nucleic acid molecule of claim 1.

8. A transgenic plant transformed with the nucleic acid molecule of claim 2.

9. The tranagenic plant of claim 7 where the plant is a monocotyledonous plant.

10. The transgenic plant of claim 7 where the plant is a dicotyledonous plant.

11. The tranagenic plant of claim 8 where the plant is a monocotyledonous plant.

12. The transgenic plant of claim 8 where the plant is a dicotyledonous plant.

* * * * *